United States Patent [19]
Giger et al.

[11] Patent Number: 5,931,780
[45] Date of Patent: Aug. 3, 1999

[54] METHOD AND SYSTEM FOR THE COMPUTERIZED RADIOGRAPHIC ANALYSIS OF BONE

[75] Inventors: Maryellen L. Giger, Elmhurst; Kunio Doi, Willowbrook, both of Ill.

[73] Assignee: Arch Development Corporation, Chicago, Ill.

[21] Appl. No.: 08/158,388

[22] Filed: Nov. 29, 1993

[51] Int. Cl.$^6$ ..................................................... A61B 5/05
[52] U.S. Cl. .......................................... 600/407; 600/437
[58] Field of Search .............................. 128/653.1, 653.2, 128/660.01, 920, 916; 382/6; 364/413.13, 413.14; 600/407, 410, 437

[56] References Cited

U.S. PATENT DOCUMENTS

| | | | |
|---|---|---|---|
| 4,851,984 | 7/1989 | Doi et al. | 382/6 |
| 4,903,203 | 2/1990 | Yamashita et al. | 128/653.1 |
| 4,907,156 | 3/1990 | Doi et al. | 382/6 |
| 4,922,915 | 5/1990 | Arnold et al. | 382/6 |
| 4,941,474 | 7/1990 | Pratt, Jr. | 128/660.01 |
| 5,133,020 | 7/1992 | Giger et al. | 382/6 |
| 5,143,069 | 9/1992 | Kwon et al. | 128/660.01 |
| 5,172,695 | 12/1992 | Cann et al. | 128/653.1 |
| 5,247,934 | 9/1993 | Wehrli et al. | 128/653.2 |
| 5,348,009 | 9/1994 | Ohtomo et al. | 128/653.1 |

FOREIGN PATENT DOCUMENTS

| | | | |
|---|---|---|---|
| 9117517 | 11/1991 | European Pat. Off. | 382/6 |

OTHER PUBLICATIONS

Chair–Li Chang et al., "Computer–aided diagnosis: Detection and Characterization of Hyperparathyroidism in Digital Hand Radiographs", Medical Physics, vol. 20, No. 1, Jul. 1993.

N. Hakim et al, "A Digital Image Processing Approach to Diagnosis of Osteoprosis", IEEE Computer Society Press, pp. 631–634, CH 22461, Feb. 1987.

Computerized Radiographic Analysis Of Osteoporosis: Preliminary Evaluation Philip Caligiuri, MD et al., Radiology, vol. 186, No. 2, pp. 471–4, 1993.

Image Feature Analysis and Computer–Aided Diagnosis In Digital Radiography: Classification Of Normal And Abnormal Lungs With Interstitial Disease In Chest Images, Shigehiko Katsuragawa, et al., Medical Physics, vol. 16, No. 1 Jan./Feb. 1989, pp. 38–44.

(List continued on next page.)

*Primary Examiner*—Brian L. Casier
*Attorney, Agent, or Firm*—Oblon, Spivak, McClelland, Maier & Neustadt, P.C.

[57] ABSTRACT

A computerized method and system for the radiographic analysis of bone structure and risk of future fracture with or without the measurement of bone mass. Techniques including texture analysis for use in quantitating the bone structure and risk of future fracture. The texture analysis of the bone structure incorporates directionality information, for example in terms of the angular dependence of the RMS variation and first moment of the power spectrum of a ROI in the bony region of interest. The system also includes using dual energy imaging in order to obtain measures of both bone mass and bone structure with one exam. Specific applications are given for the analysis of regions within the vertebral bodies on conventional spine radiographs. Techniques include novel features that characterize the power spectrum of the bone structure and allow extraction of directionality features with which to characterize the spatial distribution and thickness of the bone trabeculae. These features are then merged using artificial neural networks in order to yield a likelihood of risk of future fracture. In addition, a method and system is presented in which dual-energy imaging techniques are used to yield measures of both bone mass and bone structure with one low-dose radiographic examination; thus, making the system desirable for screening (for osteoporosis and risk of future fracture).

37 Claims, 29 Drawing Sheets

OTHER PUBLICATIONS

Image Feature Analysis and Computer–Aided Diagnosis In Digital Radiography: Effect Of Digital Parameters On The Accuracy Of Computerized Analysis Of Interstitial Disease In Digital Chest Radiographs, Shigehiko Katsuragawa et al., Medical Physics, vol. 17, No. 1, Jan./Feb. 1990, pp. 72–78.

Image Feature Analysis and Computer–Aided Diagnosis In Digital Radiography: Detection And Characterization Of Interstitial Lung Disease In Digital Chest Radiographs, Medical Physics, vol. 15, No. 3, 1988, pp. 311–319.

Computer–Aided Detection Of Diffuse Liver Disease In Ultrasound Images, Chihiro Abe, MD et al., Investigative Radiology, Jan. '92, vol. 27, pp. 71–7.

SECTORS OF POWER SPECTRUM
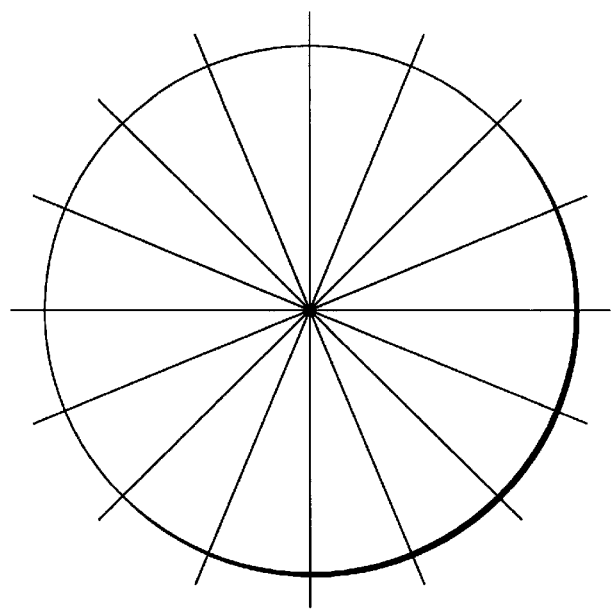
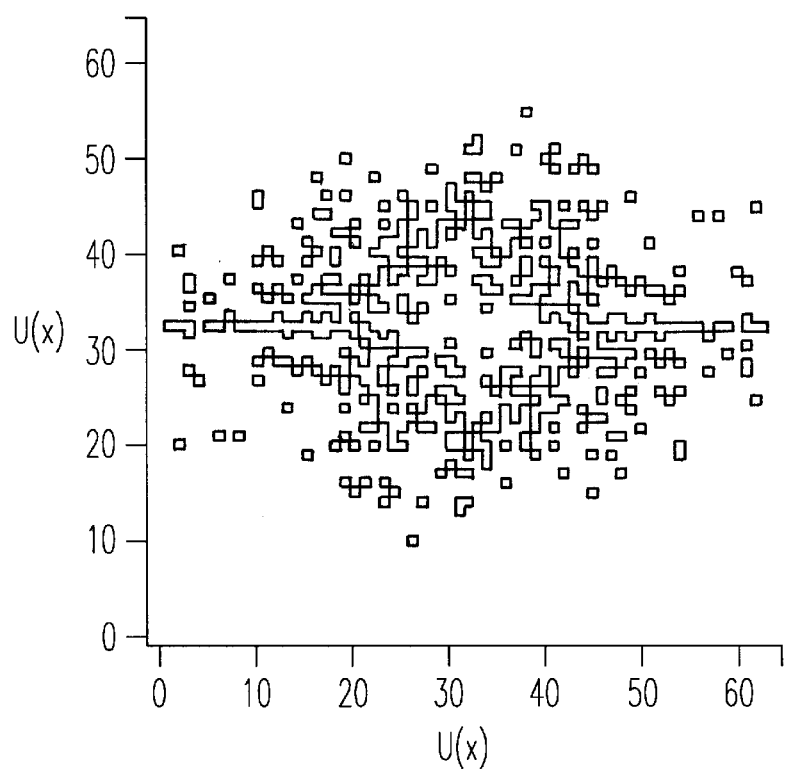
FIG. 4

FIG. 5

MEASURES OF THE BONE TEXTURE PATTERN.

| | |
|---|---|
| IRMS: | RMS VARIATION |
| R$\theta$: | ANGULAR DEPENDENCE OF RMS VARIATION |
| PRMS: | max [R$\theta$] |
| TRMS: | min [R$\theta$] |
| DRMS: | max [R$\theta$] − min [R$\theta$] |
| RRMS: | max [R$\theta$] / min [R$\theta$] |
| SDRMS: | STANDARD DEVIATION OF R$\theta$ |
| SARMS: | RELATIVE STD. DEVIATION OF R$\theta$ |
| | |
| IFMP: | 1st MOMENT OF THE POWER SPECTRUM |
| M$\theta$: | ANGULAR DEPENDENCE OF THE 1st MOMENT |
| PFMP: | max [M$\theta$] |
| TFMP: | min [M$\theta$] |
| DFMP: | max [M$\theta$] − min [M$\theta$] |
| RFMP: | max [M$\theta$] / min [M$\theta$] |
| SDFMP: | STANDARD DEVIATION OF [M$\theta$] |
| SAFMP: | RELATIVE STD. DEVIATION OF [M$\theta$] |

"HEALTHY" BONE

OSTEOPOROTIC BONE
(NOTE TRABECULAE ARE THINNED)

DIRECTIONAL PERPENDICULAR TO MAJOR TRABECULAE,
WHICH IS DETERMINED WHEN THE ANGULAR DEPENDENCE
OF THE TEXTURE MEASURES IS EXAMINED.

FIG. 20A

EFFECT OF PIXEL SIZE ON RMS VARIATION
(IN TERMS OF Az IN PREDICTING FRACTURE ELSEWHERE IN SPINE)

| SAMPLING DISTANCE (mm) | SAMPLING APERTURE (mm) | | |
|---|---|---|---|
| | 0.175 | 0.525 | 0.875 |
| 0.175 | 0.87 | 0.89 | 0.89 |
| 0.35 | 0.89 | 0.89 | 0.89 |
| 0.70 | 0.89 | 0.90 | 0.89 |

FIG. 20B

EFFECT OF PIXEL SIZE ON FIRST MOMENT OF POWER SPECTRUM
(IN TERMS OF Az IN PREDICTING FRACTURE ELSEWHERE IN SPINE)

| SAMPLING DISTANCE (mm) | SAMPLING APERTURE (mm) | | |
|---|---|---|---|
| | 0.175 | 0.525 | 0.875 |
| 0.175 | 0.89 | 0.88 | 0.90 |
| 0.35 | 0.90 | 0.88 | 0.89 |
| 0.70 | 0.81 | 0.82 | 0.86 |

FIG. 20C

EFFECT OF PIXEL SIZE ON STD. OF ANGULAR DEPENDENCE OF RMS VARIATION
(IN TERMS OF Az IN PREDICTING FRACTURE ELSEWHERE IN SPINE)

| SAMPLING DISTANCE (mm) | SAMPLING APERTURE (mm) | | |
|---|---|---|---|
| | 0.175 | 0.525 | 0.875 |
| 0.175 | 0.91 | 0.90 | 0.91 |
| 0.35 | 0.88 | 0.91 | 0.90 |
| 0.70 | 0.83 | 0.86 | 0.88 |

FIG. 20D

EFFECT OF PIXEL SIZE ON MINIMUM OF ANGULAR DEPENDENCE OF THE FIRST MOMENT
(IN TERMS OF Az IN PREDICTING FRACTURE ELSEWHERE IN SPINE)

| SAMPLING DISTANCE (mm) | SAMPLING APERTURE (mm) | | |
|---|---|---|---|
| | 0.175 | 0.525 | 0.875 |
| 0.175 | 0.91 | 0.90 | 0.90 |
| 0.35 | 0.91 | 0.89 | 0.91 |
| 0.70 | 0.82 | 0.81 | 0.80 |

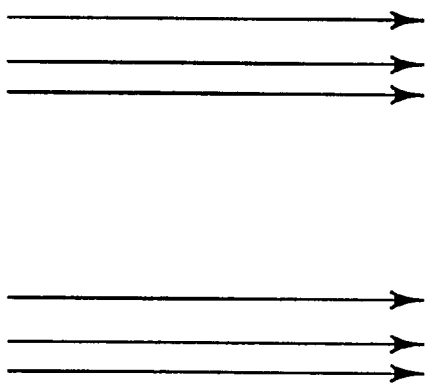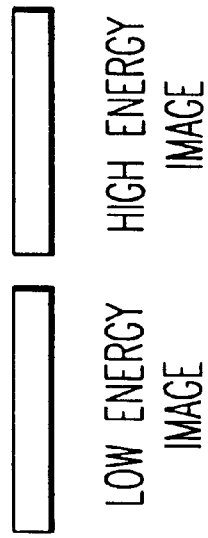
FIG.22B TWO EXPOSURE
LOW ENERGY IMAGE
HIGH ENERGY IMAGE
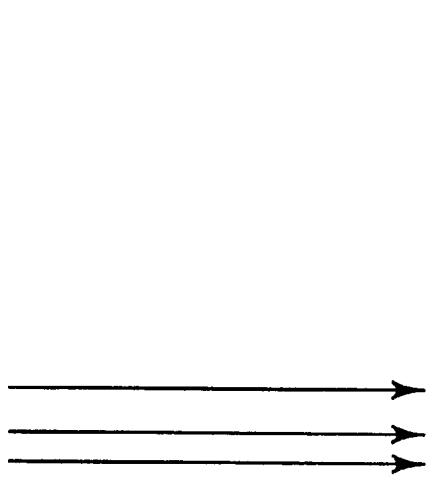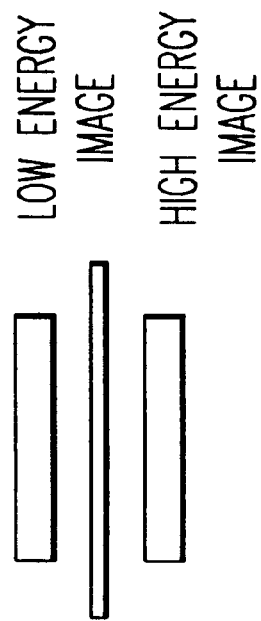
FIG.22A ONE SHOT SINGLE EXPOSURE
LOW ENERGY IMAGE
HIGH ENERGY IMAGE ROIs FOR CALIBRATION

METHOD AND SYSTEM FOR THE COMPUTERIZED RADIOGRAPHIC ANALYSIS OF BONE The present invention was made in part with U.S. Government support under NIH grants/contracts CA48985 and CA47043, Army grant/contract DAMD 17-93-J-3021, and American Society grant/contract FRA-390. The U.S. Government has certain rights in the invention.

BACKGROUND OF THE INVENTION

1. Field of the Invention

The invention relates generally to a method and system for the computerized radiographic analysis of bone structure. Specific applications are given for the analysis of the trabecular mass and bone pattern for the assessment of osteoporosis and as a predictor of risk of fracture. Novel techniques involve a directional analysis of the Fourier spectrum relative to many texture measures. Additional techniques include the a one-shot dual energy exposure for the assessment of bone mass while simultaneously obtaining an image for the texture analysis for bone structure.

2. Discussion of the Background

Osteoporosis is a widespread medical condition that affects about 15–20 million people in the United States and accounts for about 1.3 million new fractures per year in people greater than 45 years of age. Osteoporosis manifests as a loss in bone mass, a tendency to fracture and as a structural alteration of bone. Quantitative measures of bone mass serve as important diagnostic indicators for determining the risk of fracture and in following the progress of patients on therapy for osteoporosis. The most widely used methods of assessing bone mass are by bone mineral densitometry (BMD) that involves dual photon absorptiometry with either an x-ray or nuclear source, and quantitative computed tomography. These methods are very accurate in determining bone mass, which has been shown to be a very good predictor of fracture risk in osteoporosis. There is, however, considerable overlap of the measurements of BMD for patients with osteoporosis who have, or go on to have atraumatic fractures compared to age-matched controls who do not have, or do not go on to have, atraumatic fractures. In addition to bone mass, bone structure is probably also important in determining the mechanical strength of bone and thus fracture risk. A few preliminary studies have been performed in relating certain textural measures to bone structure.

SUMMARY OF THE INVENTION

Accordingly, an object of this invention is to provide a computerized method and system for the radiographic analysis of bone structure and risk of future fracture.

Another object of this invention is to provide a method and system for texture analysis for use in quantitating the bone structure and risk of future fracture.

Another object of this invention is to provide a method and system for incorporating directionality information in the analysis of the bone structure (texture).

Another object of this invention is to provide a method and system for using dual energy imaging in order to obtain measures of both bone mass and bone structure with one exam.

These and other objects are achieved according to the invention by providing a new and improved method and system for the analysis of bone structure and future risk of fracture. Specific applications are given for the analysis of regions within the vertebral bodies on conventional spine radiographs. Techniques include novel features that characterize the power spectrum of the bone structure and allow extraction of directionality features with which to characterize the spatial distribution and thickness of the bone trabeculae. These features are then merged using artificial neural networks in order to yield a likelihood of risk of future fracture. In addition, a method and system is presented in which dual-energy imaging techniques are used to yield measures of both bone mass and bone structure with one low-dose radiographic examination; thus, making the system desirable for screening (for osteoporosis and risk of future fracture).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a schematic diagram illustrating the power spectrum (with sectors indicated) obtained from the Fourier transform of the corrected ROI image data.

FIG. 5 is a schematic diagram listing the various measures including directionality measures obtained from the power spectrum of the image data.

FIG. 20 contains tables showing the effect of pixel size on four of the texture measures in terms of Az in predicting fracture elsewhere in the spine.

FIG. 22 is a schematic diagram illustrating two possible methods of obtaining the dual-energy radiographic images.

DETAILED DESCRIPTION OF THE PREFERRED EMBODIMENTS

Figure 1:
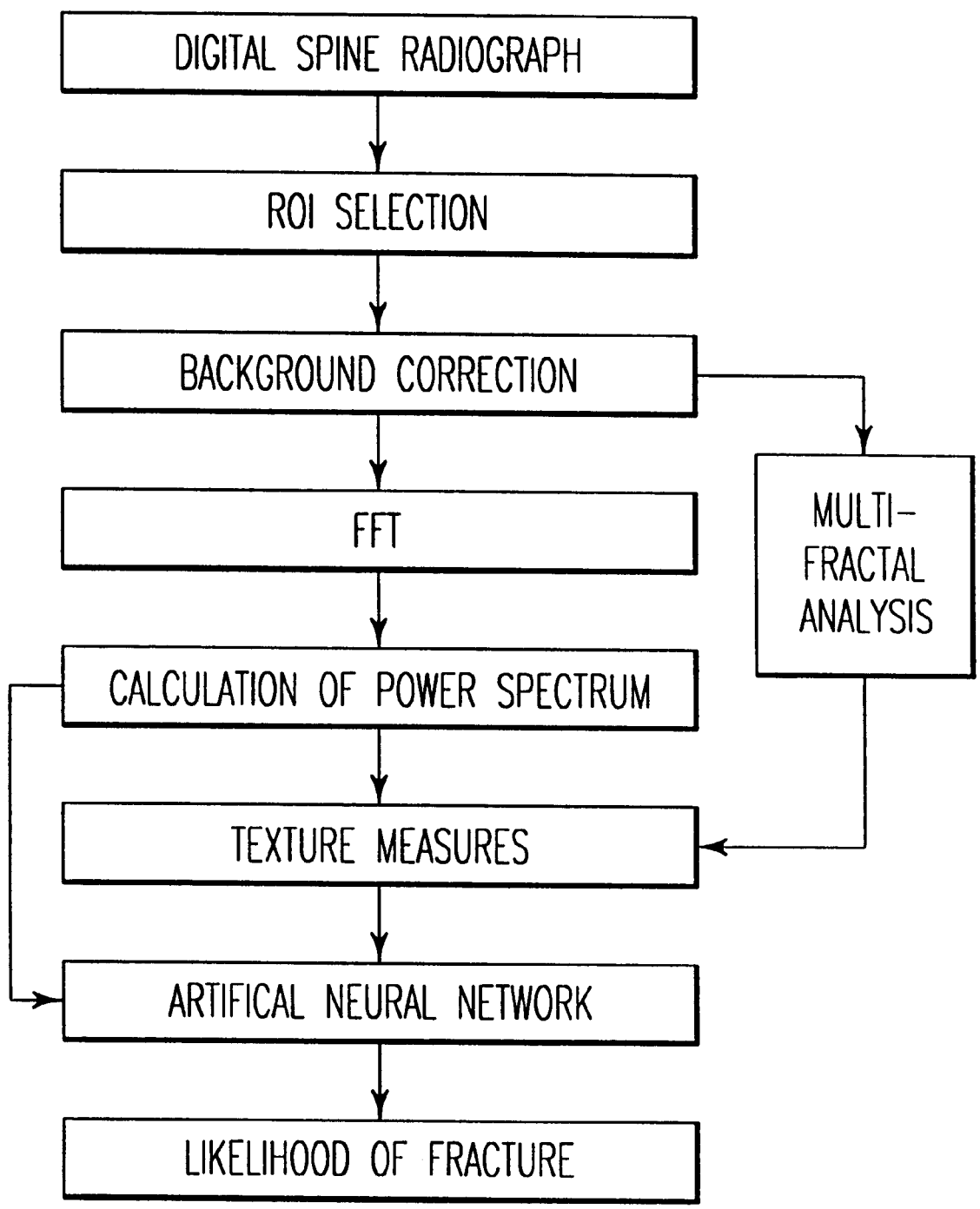
FIG. 1 is a schematic diagram illustrating the method for analysis of bone structure according to the invention.

Referring now to the drawings, and more particularly to FIG. 1 thereof, a schematic diagram of the analysis of bone structure is shown. In this example, the aim is to extract the characteristics of the bone trabeculae using texture analysis of image data from digital images of bony parts of the body such as the spine. The overall scheme includes an initial acquisition of a radiograph of the spine (step 10) and digitization (step 20) (or a direct digital acquisition of the radiographic image of the spine). A region of interest (ROI) is then placed over a vertebral body on the image and the corresponding image data are stored in memory (step 30). Background trend correction (step 40) is performed to yield the underlying fluctuations, i.e., the trabecular pattern. The image data in the ROI are then input to a Fast Fourier Transform (step 50) and the power spectrum is calculated (step 60). Various textures measures are calculated from the power spectrum data (step 70) and these are merged using an artificial neural network (step 80) to yield a likelihood of risk of future fracture (step 80). Other texture analyses can be used such as fractal analysis.

Figure 2A:
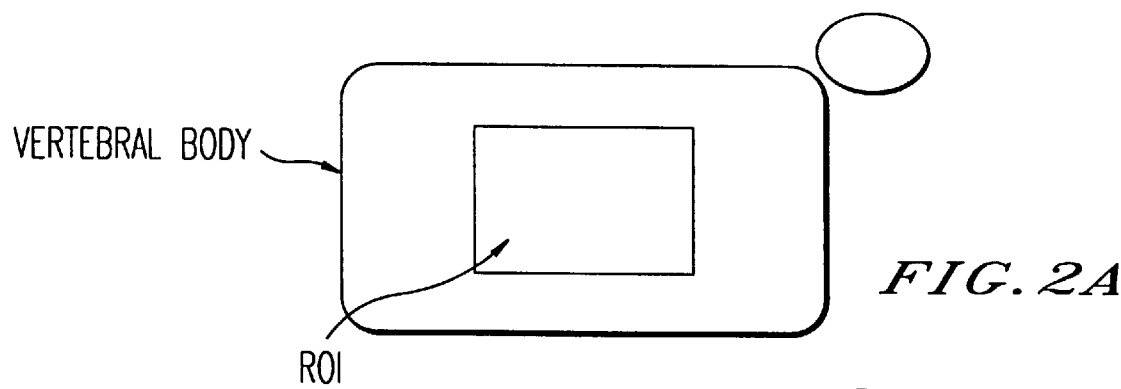
FIG. 2 is a schematic diagram illustrating the placement of ROIs on the vertebral bodies in digital lumbar spine images.
Figure 2B:
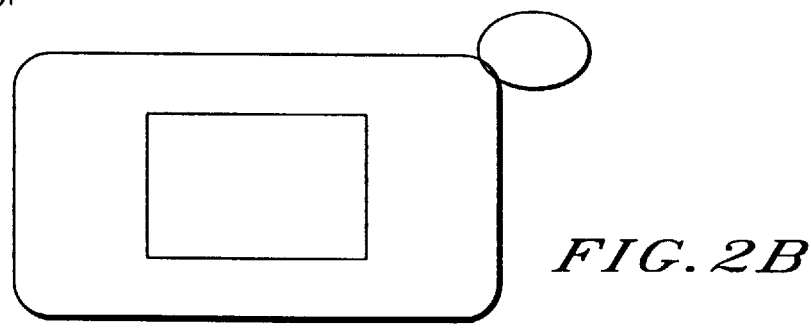
Figure 2C:
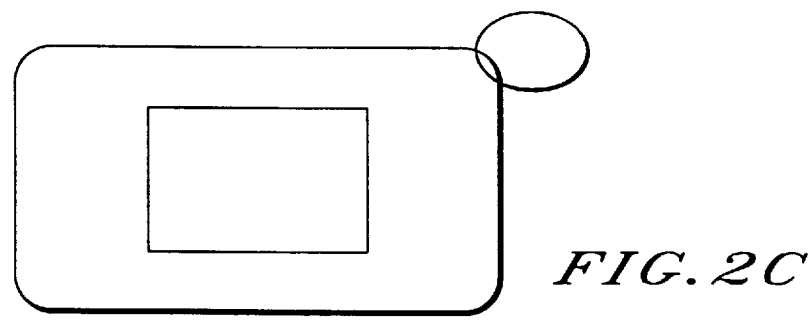

FIG. 2 illustrates further the placement of ROIs on the vertebral bodies in the digital lumbar spine images. Shown here are ROIs, 64 pixels by 64 pixels in size, placed at the L2, L3, and L4 levels on the spine. Placement is performed such that the ROIs avoid overlapping edges, bowel gas, and soft tissue folds. In general, ROIs placed at the L3 level had the least interference from edges and bowel gas, and thus precise placement of the ROIs within the vertebral body is not necessary at the L3 level.

Figure 3:
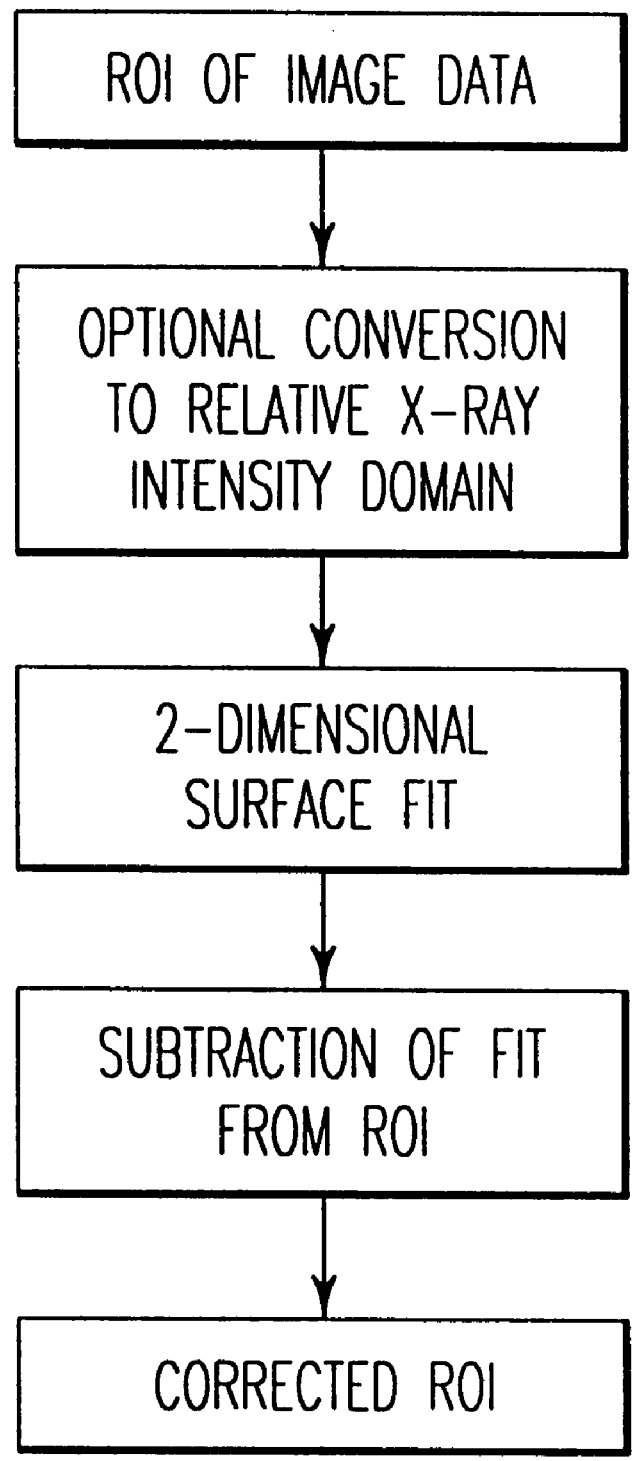
FIG. 3 is a schematic illustrating corrections for the possible nonlinear nature of the detector system's characteristic response (H & D curve for film) and for background trend within the ROI image data.

FIG. 3 illustrates the corrections for the possible nonlinear nature of the detector's characteristic response (the H & D curve for radiographic films as detector) and for the background trend within the ROI image data. Background trend correction is necessary since the variation in optical density within the ROI in spine images includes that due to the gross anatomy of the human body and to the presence of bowel gas (background trends) and that due to the fine underlying texture which is related to the trabecular pattern of the bone. The nonuniform background trend can be determined using a 2-dimensional surface fitting technique (such as one with a second degree polynomial function). The fitted trend is subtracted from each ROI in order to yield the underlying fluctuations, i.e., the trabecular pattern.

FIG. 4 illustrates the power spectrum of ROI image data. The axes are in terms of spatial frequencies. It should be noted that strictly speaking, however, the power spectrum needs to be determined from an ensemble average of the square of the Fourier transform over an infinitely large area. The sectors indicate the method used individing the power spectrum into pie-shaped sections. Texture measures are calculated for the entire power spectrum as well as for the individual sectors, thus, yielding directionality measures. The power spectra of the trabecular bone pattern may contain low-frequency components due to some residual uncorrected background trend and very high-frequency components due to radiographic mottle in the original bone radiographic image. Thus, the power spectra may be filtered by the human visual system response function with acts as a band-pass filter.

FIG. 5 is a schematic diagram listing the various measures obtained from the power spectrum data. The texture analysis process initially involves two measures: the root-mean-square (RMS) variation (R) and the first moment of the filtered power spectrum (M), which represent the magnitude and the coarseness of trabecular pattern, respectively. These measures are given by $$R = \sqrt{\int_{-\infty}^{\infty}\int_{-\infty}^{\infty} [V^2(u,v)] |F(u,v)|^2 \, du \, dv}$$

$$M = \frac{\int_{-\infty}^{\infty}\int_{-\infty}^{\infty} \sqrt{u^2+v^2} \, [V^2(u,v)] |F(u,v)|^2 \, du \, dv}{\int_{-\infty}^{\infty}\int_{-\infty}^{\infty} [V^2(u,v)] |F(u,v)|^2 \, du \, dv}$$

where V(u,v) and F(u,v) correspond to the visual system response and the Fourier transform of the trabecular pattern, respectively. Higher moments of the power spectra can also be calculated. Higher moments are not conceptualized visually as easily as the rms variation and first moment values, however.

Due to the strong directional appearance of trabecular patterns, the RMS variation and various moments of the power spectra will be calculated also as a function of angle in the Fourier domain as given below by the inequalities and tables.

Angular dependence of RMS variation:

$$R_\theta(\theta_1 \le \theta < \theta_2) = \sqrt{\sum_m \sum_n |F_{m,n}|^2} \text{ for } \theta_1 \le \tan^{-1}\left(\frac{n}{m}\right) < \theta_2$$

Angular dependence of First Moment of the Power Spectrum:

$$M_\theta(\theta_1 \le \theta < \theta_2) = \frac{\sum_m \sum_n \sqrt{m^2+n^2} \, |F_{m,n}|^2}{\sum_m \sum_n |F_{m,n}|^2} \text{ for } \theta_1 \le \tan^{-1}\left(\frac{n}{m}\right) < \theta_2$$

Figure 6A:
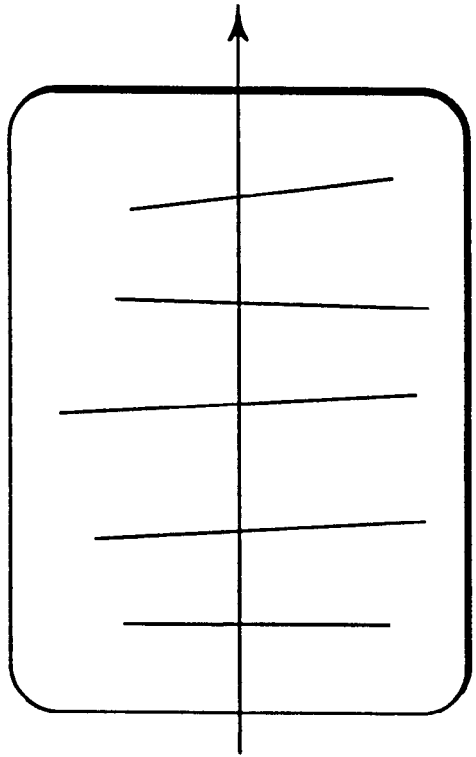
FIG. 6 is a schematic illustrating some of the texture measures for non-osteoporotic ("healthy") bone and for diseased bone.
Figure 6B:
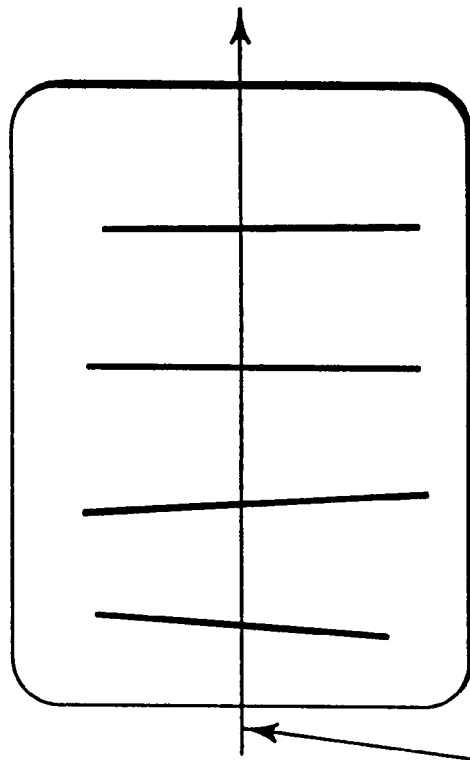

The angular dependence of the two measure (RMS and FMP) are examined by dividing the power spectrum into several sectors and performing the summations within each sector. From studies, we have found that those with fracture elsewhere in the spine exhibit a higher minimum value of the angular dependence of FMP. By taking the minimum value we force the directionality measure (i.e., perpendicular to the trabeculae) for normal patients since the bone trabeculae without osteoporosis is assumed to not show a "washed-out" appearance and thus the directionality is strong as schematically shown in FIG. 6. Since the trabeculae are not "washed-out" for normal patients, their spatial distribution would contain lower frequency structures in a direction perpendicular to the trabeculae. Osteoporotic patients would tend to exhibit a more isotropic distribution due to the washed-out appearance of the trabeculae. Edge gradient analysis on the ROI data can also be performed to extract the direction perpendicular to the major trabeculae. The angle exhibiting the largest cumulative edge gradient is expected to indicate the direction perpendicular to the major trabeculae within the ROI. In addition, due to the possibility that quantom mottle and x-ray scatter may "hide" the underlying texture pattern of the bone trabeculae, the power spectra of uniform tissue regions within the medical image are also determined and used to normalize the power spectra obtained from the ROIs in the bony regions, prior to calculation of the texture measures. These analyses are expected to be useful in analyzing both the primary (approximately horizontal) trabeculae and the secondary (approximately vertical) trabeculae.

Figure 7:
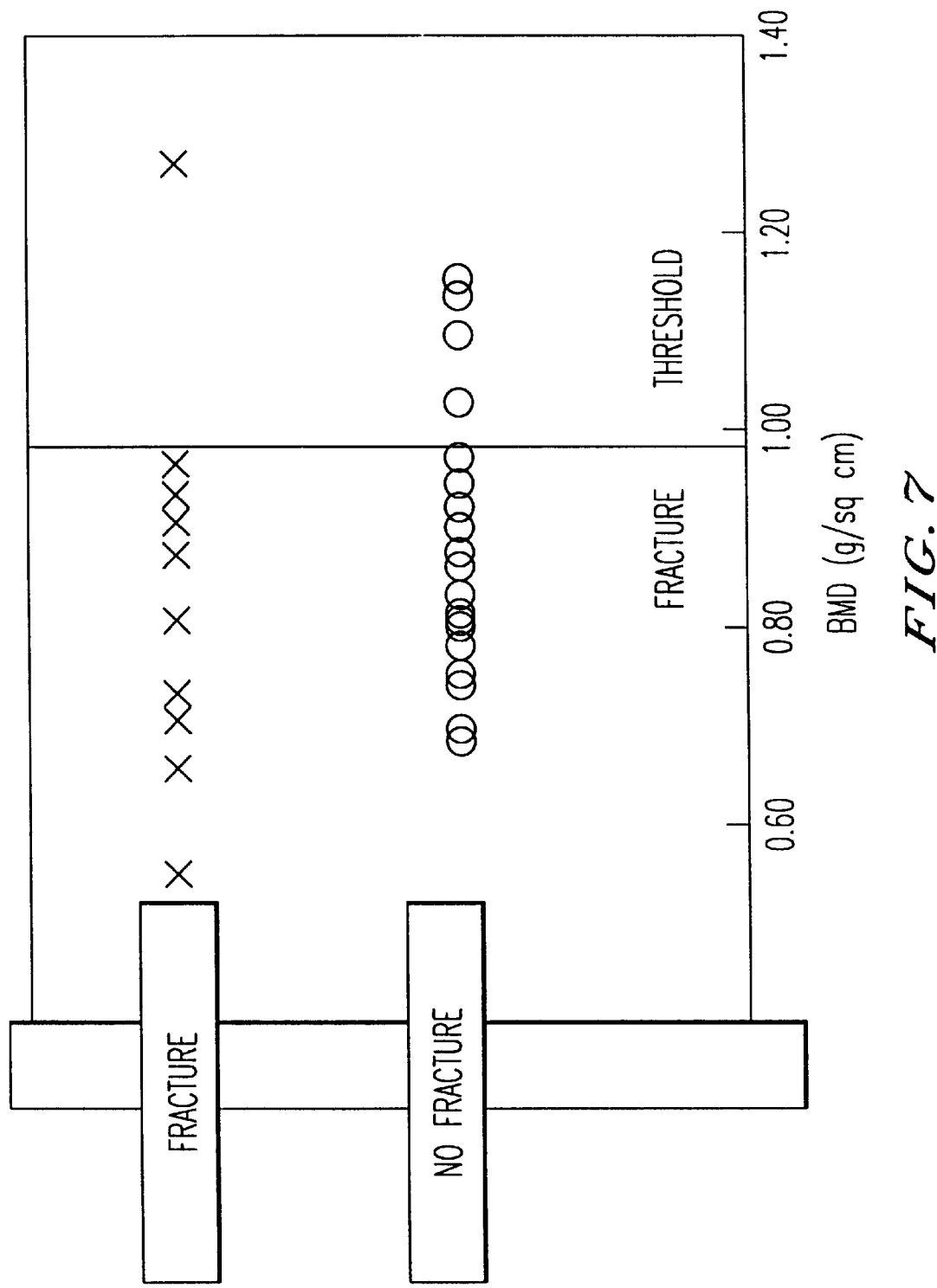
FIG. 7 is a graph showing measures of bone mass for 43 patients: some with a fracture elsewhere in the spine and some without fracture.

Studies were done using 43 patient cases in which some had a fracture elsewhere in the spine and some did not. This method for evaluation was used since the texture measures here are being examined at one point in time and it has been shown that the presence of pre-existing vertebral body fractures is a powerful predictor of future risk for vertebral body fracture. FIG. 7 is a graph showing the distribution of BMD measures (bone mass) for patients with fracture elsewhere in the spine and for those without fracture. Notice that the BMD values are low in nearly all the fracture cases as expected; most of the nonfracture cases also, however, have low BMD values. Thus, demonstrating the need for a measure with higher specificity.

Figure 8:
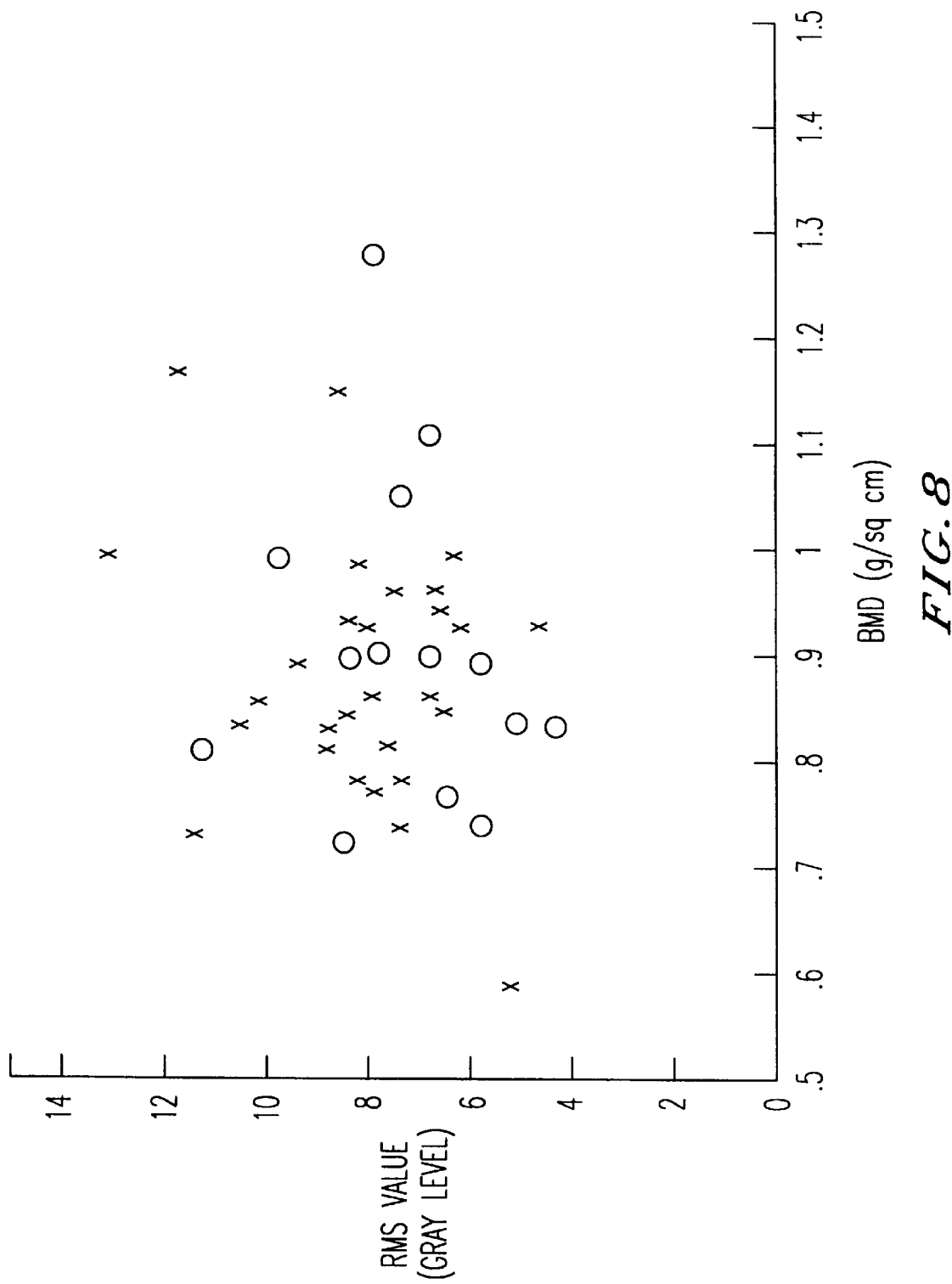
FIG. 8 is a graph showing the relationship between BMD measures (bone mass) and RMS variation (bone structure) for patients: some with a fracture elsewhere in the spine and some without fracture.
Figure 9:
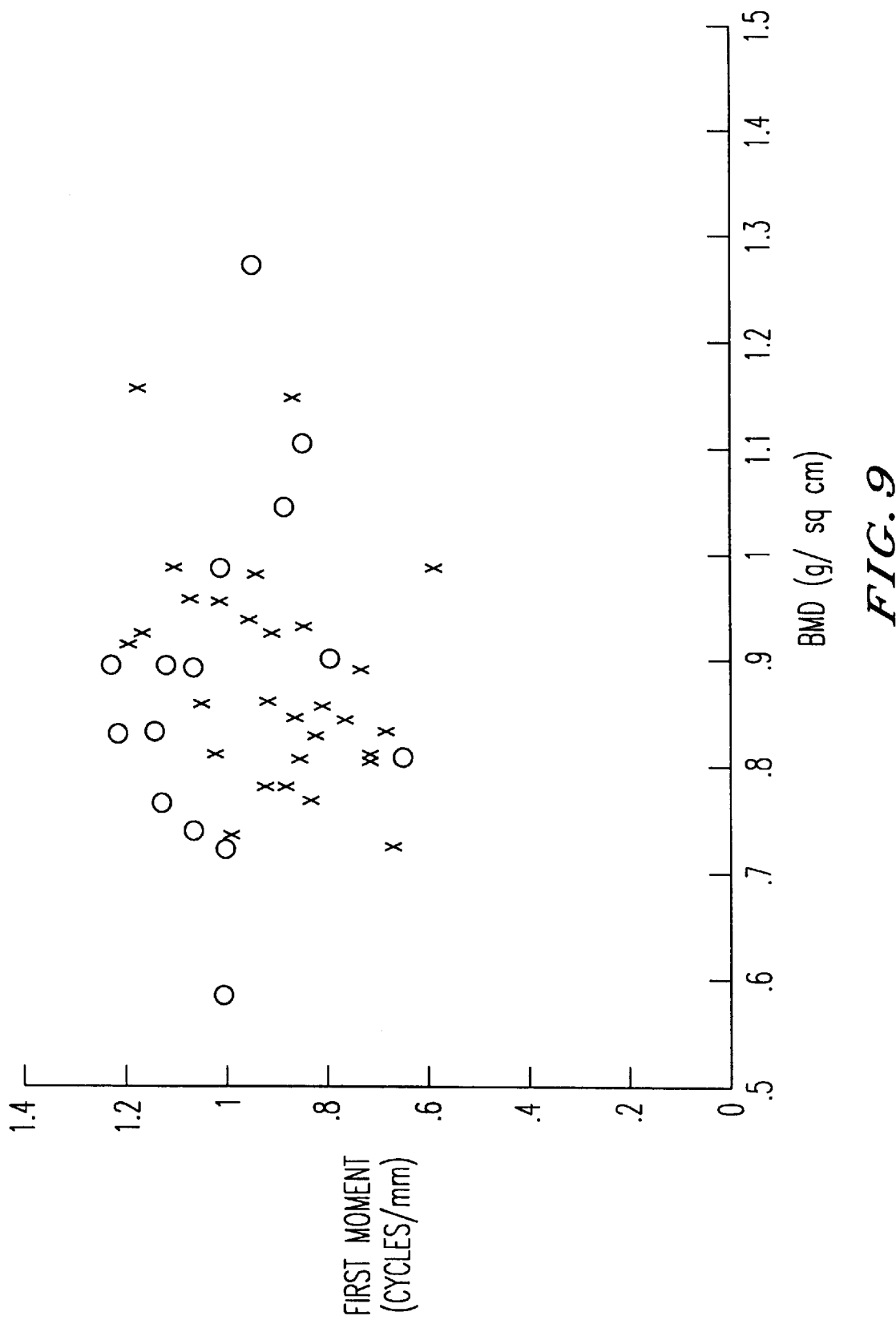
FIG. 9 is a graph showing the relationship between BMD measures (bone mass) and first moment of the power spectrum (bone structure) for patients: some with a fracture elsewhere in the spine and some without fracture.

FIGS. 8 and 9 demonstrate the relationships between BMD measures (bone mass) and the RMS variation for the same patients and between BMD and the first moment of the power spectrum. It is apparent that there is not a strong correlation between bone mass and bone structure using at least these measures for bone mass and bone structure. Note that in the following example, normalization of the power spectra was not included.

Figure 10:
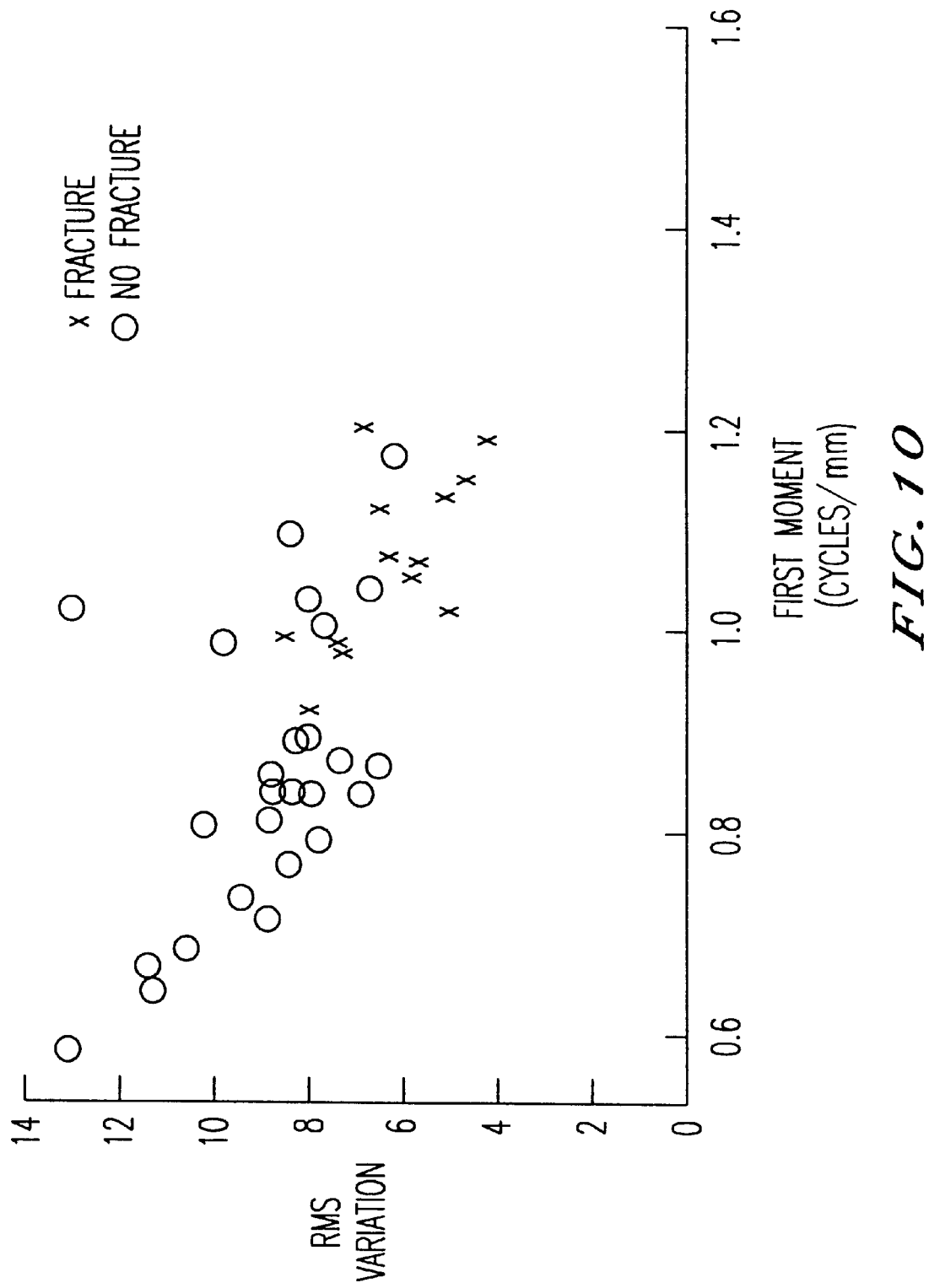
FIG. 10 is a graph illustrating the relationship between RMS variation and first moment of the power spectrum for ROIs selected from the L3 level for patients with and without fracture elsewhere in the spine.
Figure 11:
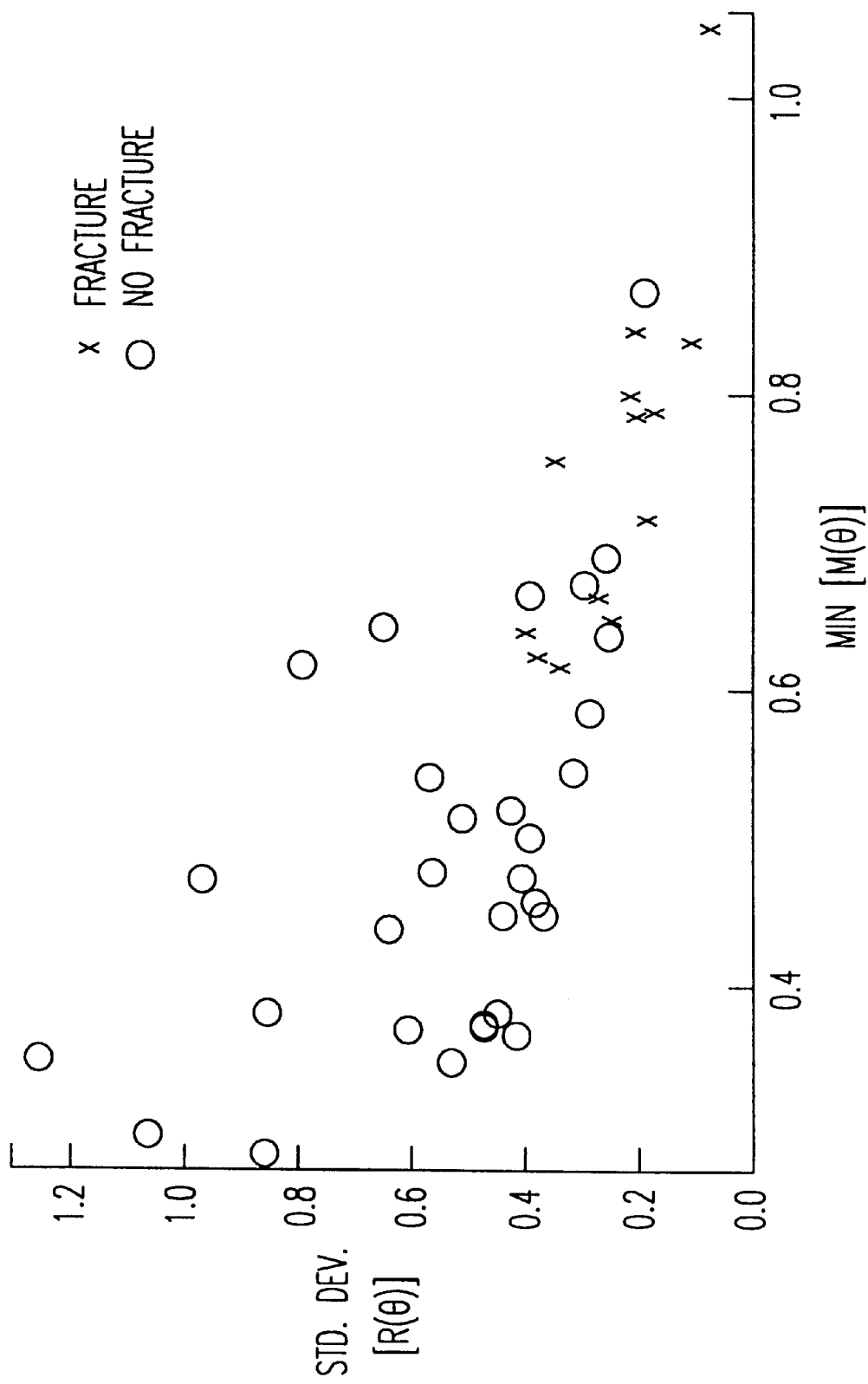
FIG. 11 is a graph illustrating the relationship between the standard deviation of the angular dependence of the RMS variation and the minimum value of the angular dependence of the first moment of the power spectrum for ROIs selected from the L3 level for patients with and without fracture elsewhere in the spine.

FIG. 10 is a graph illustrating the relationship between the RMS variation and the first moment of the power spectrum for ROIs selected from the L3 level for patients with and without fractures elsewhere in the spine. It is apparent that patients with fractures elsewhere in the spine tend to have a high first moment measure and a low RMS variation. FIG. 11 is a graph illustrating the relationship between the standard deviation of the angular dependence of the RMS variation and the minimum value of the angular dependence of the first moment of he power spectrum for ROIs selected from the L3 level for patients with and without fractures elsewhere in the spine.

Figure 12:
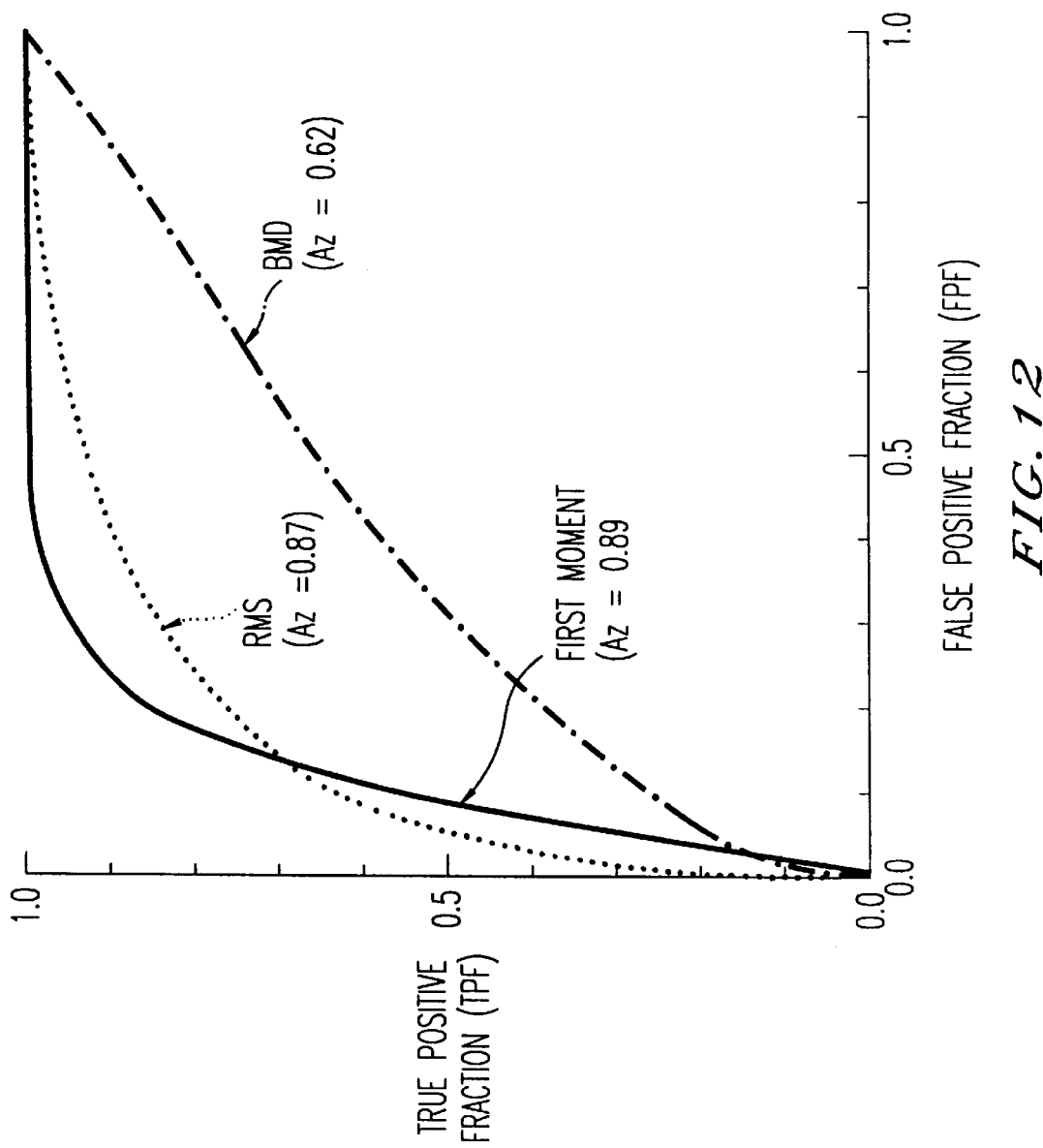
FIG. 12 is a graph showing ROC curves calculated for the measures of bone mass (BMD), RMS variation and first moment of the power spectrum.
Figure 13:
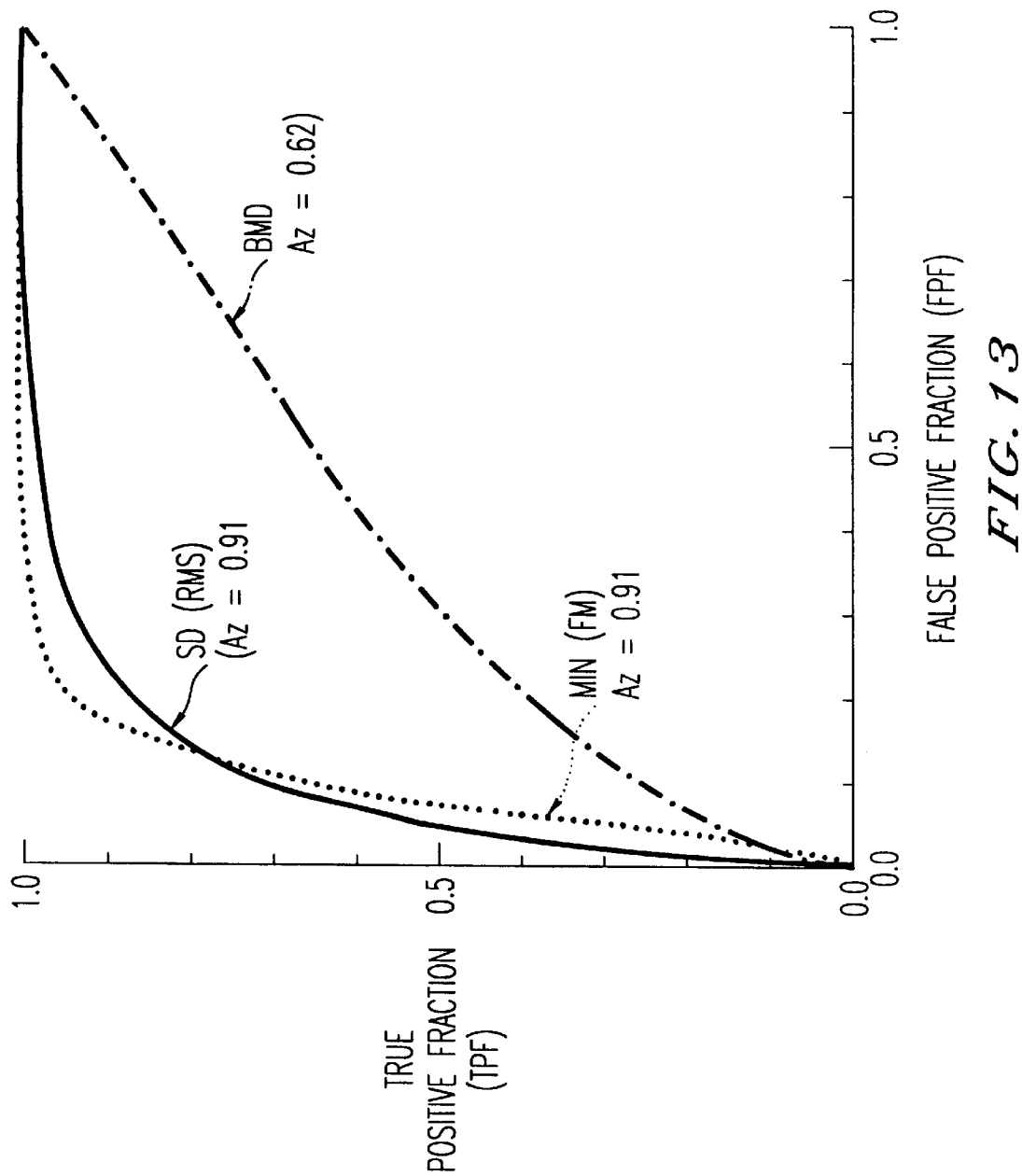
FIG. 13 is a graph showing ROC curves calculated for the measures of bone mass (BMD), the standard deviation of the angular dependence of the RMS variation and the minimum value of the angular dependence of the first moment of the power spectrum.

FIG. 12 is a graph showing ROC curves calculated for the measures of bone mass (BMD), RMS variation and first moment of the power spectrum. Here the ROC analysis was performed with respect to the task of determining whether or not the patient had a fracture elsewhere in the spine. The Az values (area under the ROC curve) for RMS variation and the first moment are superior when compared to the Az value for the measure of bone mass (BMD). FIG. 13 is a graph showing ROC curves calculated for the measures of bone mass (BMD), the standard deviation of the angular dependence of the RMS variation and the minimum value of the angular dependence of the first moment of the power spectrum.

Figure 14:
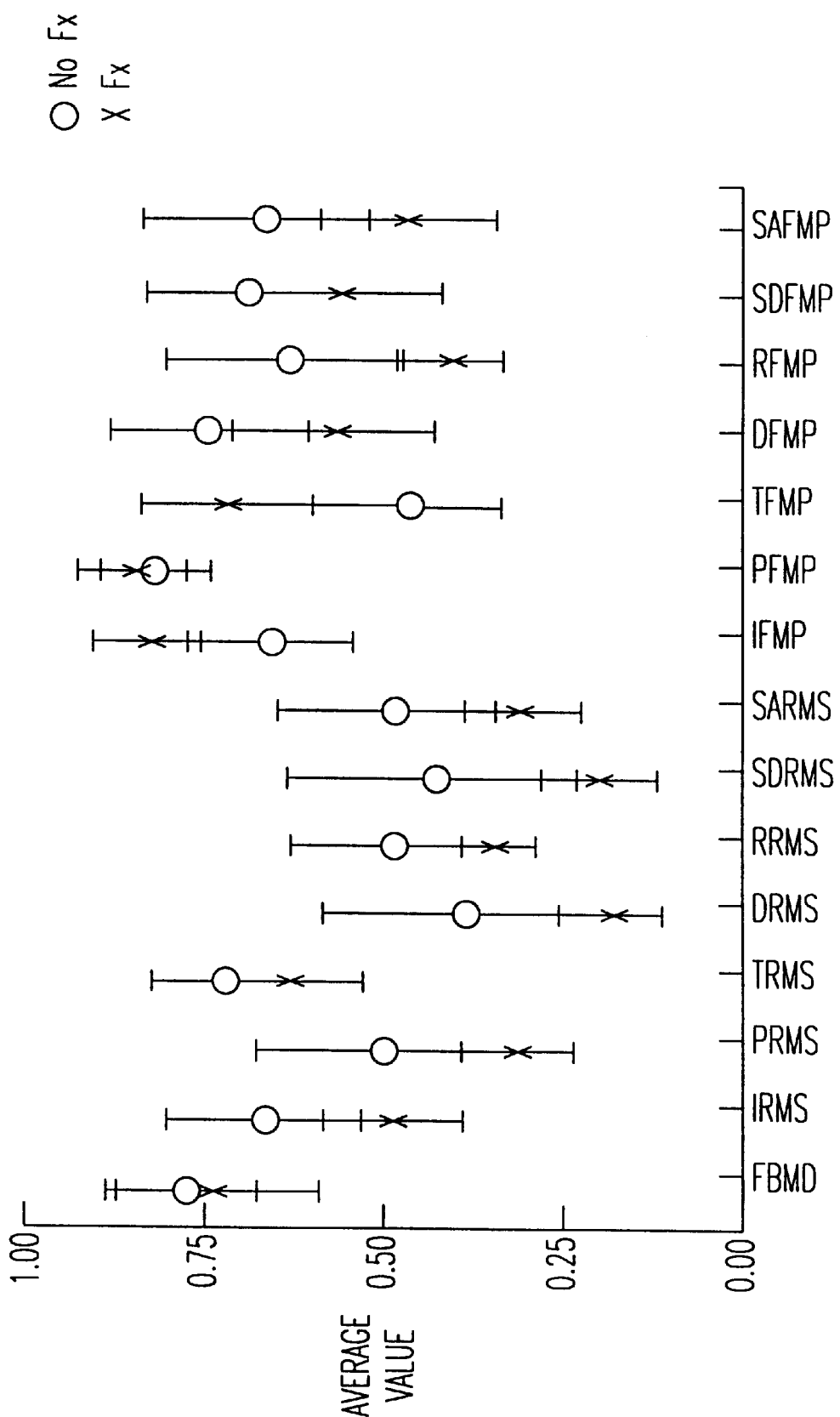
FIG. 14 is a graph showing the average values for the texture measures for cases with fracture elsewhere in the spine and for cases without fracture.
Figure 15:
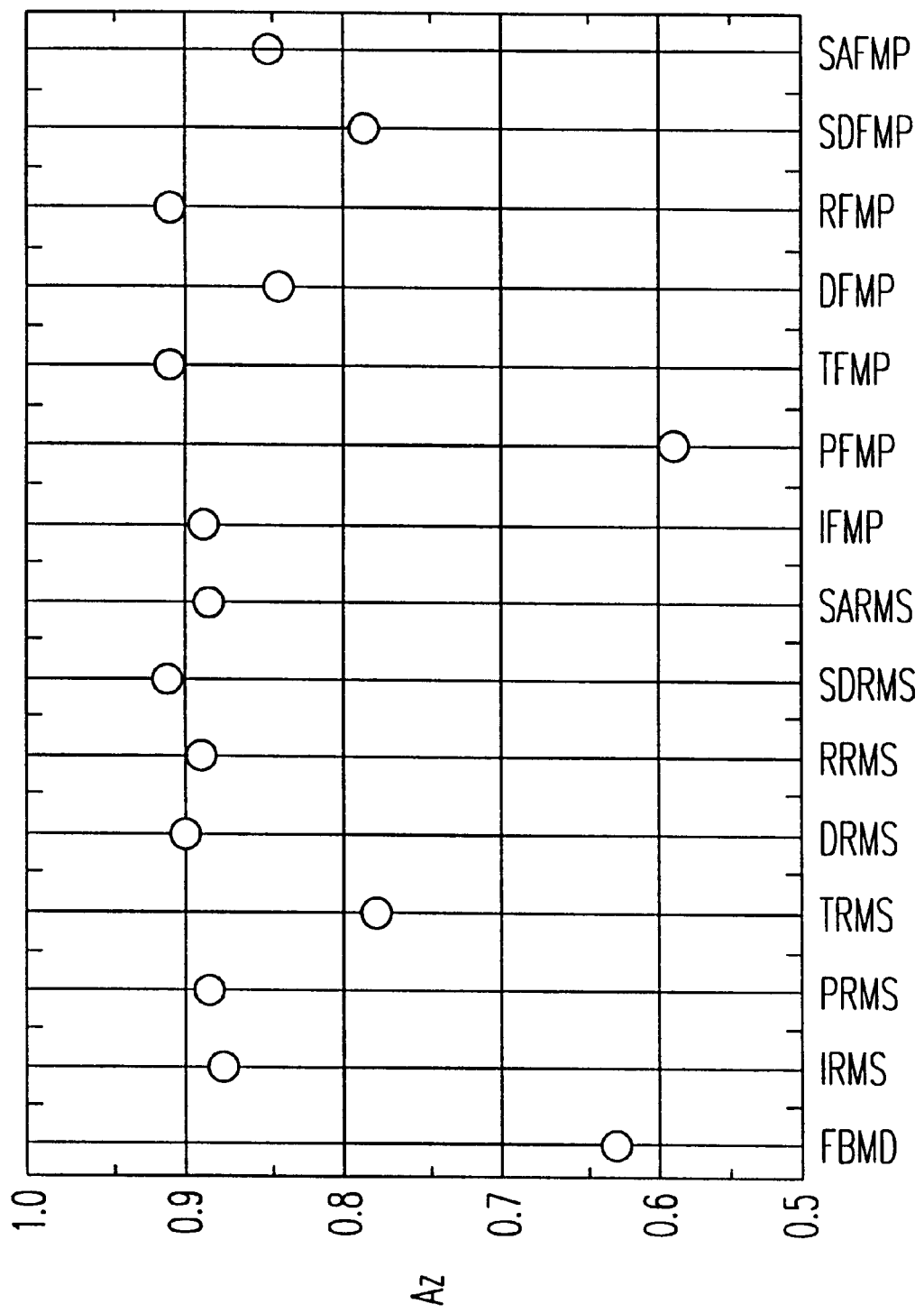
FIG. 15 is a graph indicating the performance of the individual texture measures in the task of distinguishing those cases with fracture elsewhere in the spine from those without fracture.

FIG. 14 is a graph showing the average values for the texture measures for cases with fracture elsewhere in the spine and for cases without fracture. Note that the values have been normalized between 0 and 1. FIG. 15 is a graph indicating the performance of the individual texture measures in the task of distinguishing those cases with fracture elsewhere in the spine from those without fracture. Note that higher the Az value the better the performance.

Figure 16:
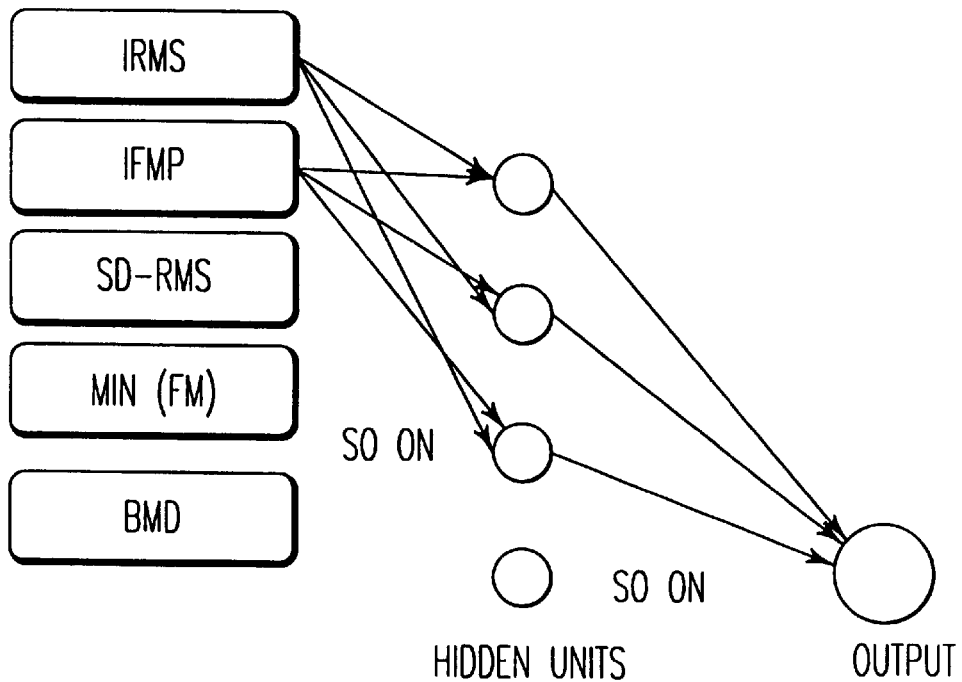
FIG. 16 is a schematic diagram of the artificial neural network used in merging the various bone structure features into a likelihood of risk of future fracture.

Once the texture measures are calculated, they can be merged using an artificial neural network in order to yield a likelihood of future risk of fracture. FIG. 16 is a schematic diagram of the artificial neural network used in merging the various bone structure features into a likelihood of risk of future fracture.

Figure 17:
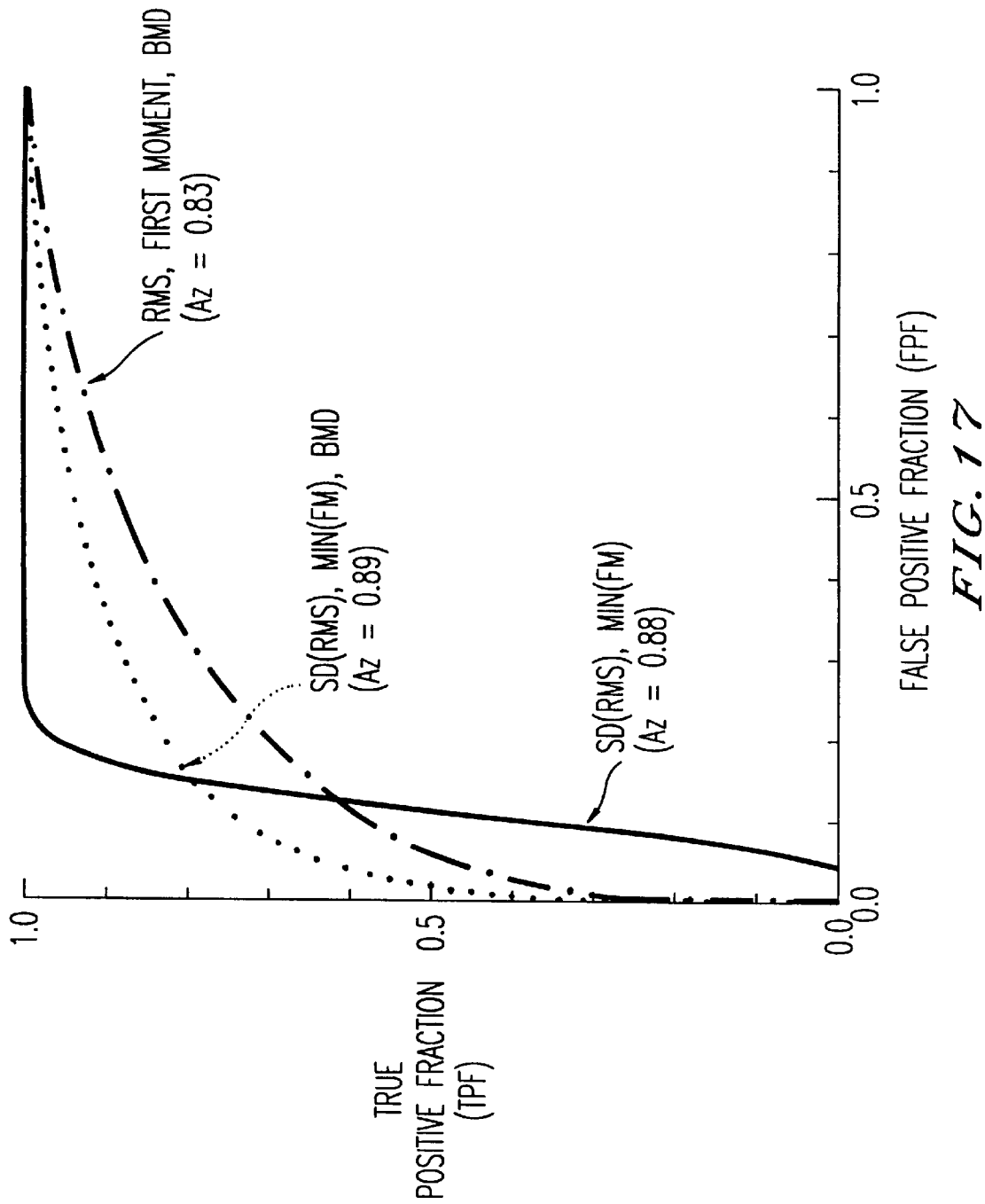
FIG. 17 is a graph showing ROC curves calculated for three neural network combinations. Two of the combinations include measures of both bone mass and bone structure; one of the combinations includes only measures of bones structure.

FIG. 17 is a graph showing ROC curves calculated for three neural network combinations. Two of the combinations include measures of both bone mass and bone structure; one of the combinations includes only measures of bone structure.

Figure 18A:
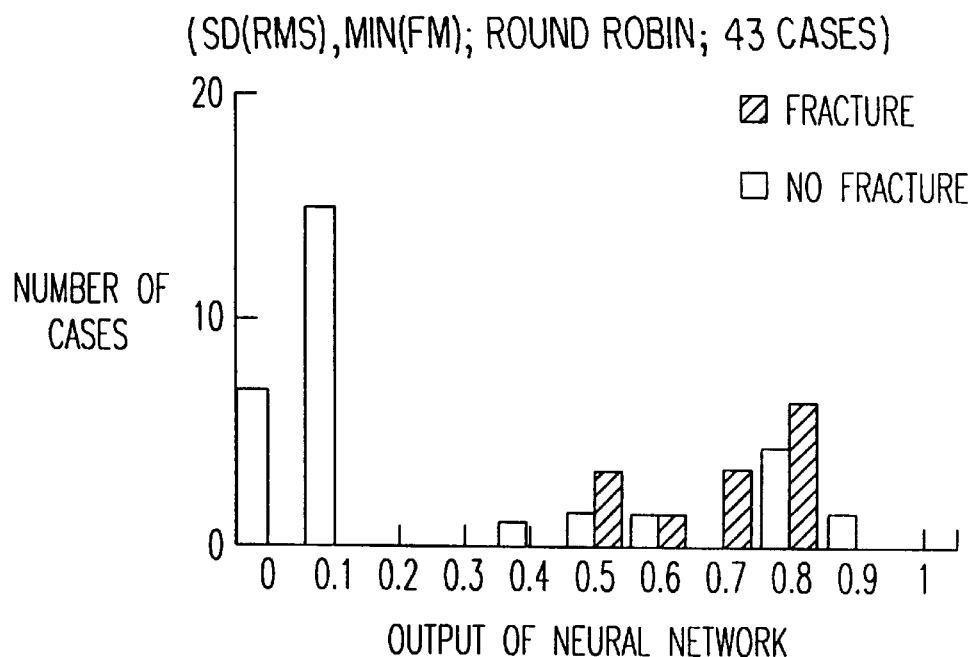
FIG. 18 shows two graphs indicating the histogram (distribution) of the output values from the artificial neural network for two of the neural network combinations.
Figure 18B:
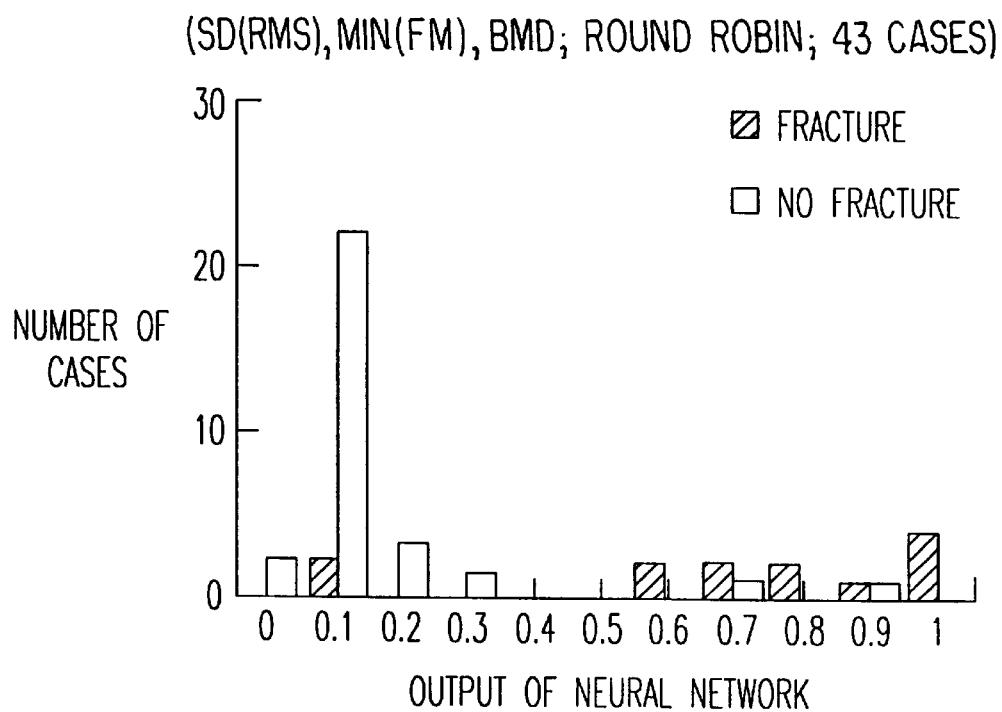

FIG. 18 shows two graphs indicating the histogram (distribution) of the output values from the artificial neural network for two of the neural network combinations. The output from the neural network can be thresholded so that only cases with a certain value from the neural network output are noted as having a higher risk for future fracture.

Figure 19:
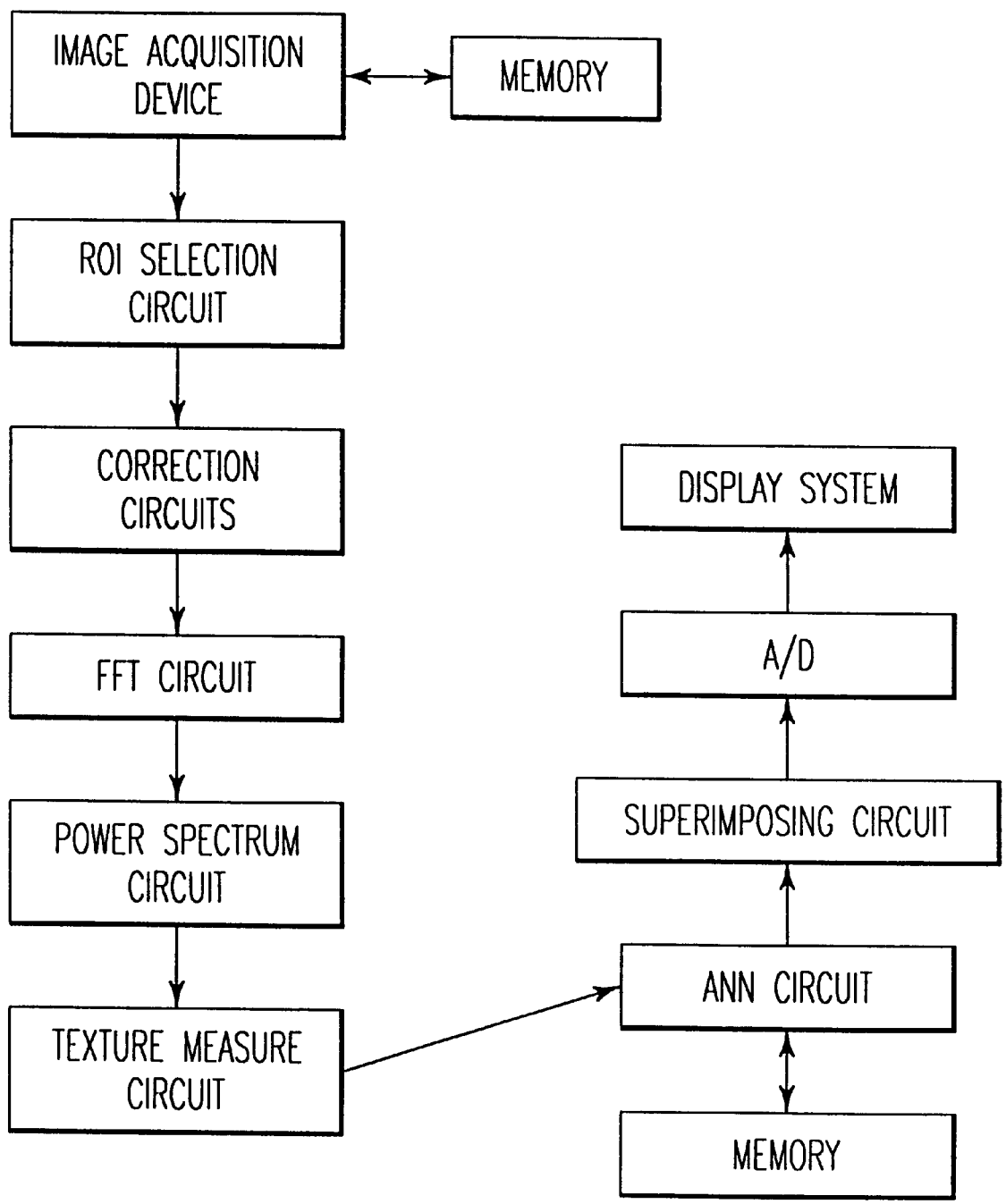
FIG. 19 is a schematic block diagram illustrating a system for implementing the method for the computerized, radiographic analysis of bone structure and risk of future fracture.

FIG. 19 is a more detailed schematic block diagram illustrating a system for implementing the method of the invention for analysis of the bone trabecular structure. Referring to FIG. 19, radiographic images of an object are obtained from an image acquisition device and input to the system 100. Each bone image is digitized and put into memory (1001). If the radiographic image is obtained with a direct digital device then there is no need for digitization. The image data is first passed through the ROI selection circuit (1002), the nonlinear detection system correction circuit (1003) and the background trend correction circuit (1004). The data is passed to the FFT circuit (1005) and the power spectrum circuit (1006). Power spectrum data are passed to the texture measure circuit (1007) and to the optional ANN circuit (1008) in order to determine the likelihood for risk of future fracture, during which time the data are retained in image memory (1009). In the superimposing circuit (1010) the results are either superimposed onto images, stored in file format, or given in text format. The results are then displayed on the display system (1020) after passing through a digital-to-analog converter (1030).

The particular image acquisition system used may affect the texture measures, so the ability of the computerized scheme to assess osteoporosis and risk of fracture as a function of pixel size of the digitization system was investigated. Use of a smaller pixel size allows higher spatial frequency components to be examined. The results shown earlier were obtained from digitization of film at a pixel of 0.175 mm with 10-bit quantization. If the texture measures can still be reliably obtained at larger pixel size then direct digital systems for imaging the bone will be more easily produced. FIG. 20 contains tables showing the effect of pixel size on four of the texture measures in terms of Az in predicting fracture elsewhere in the spine. Results are given for variations in the aperture size (blur) and sampling distance for the same 43 cases used in the earlier examples.

Figure 21:
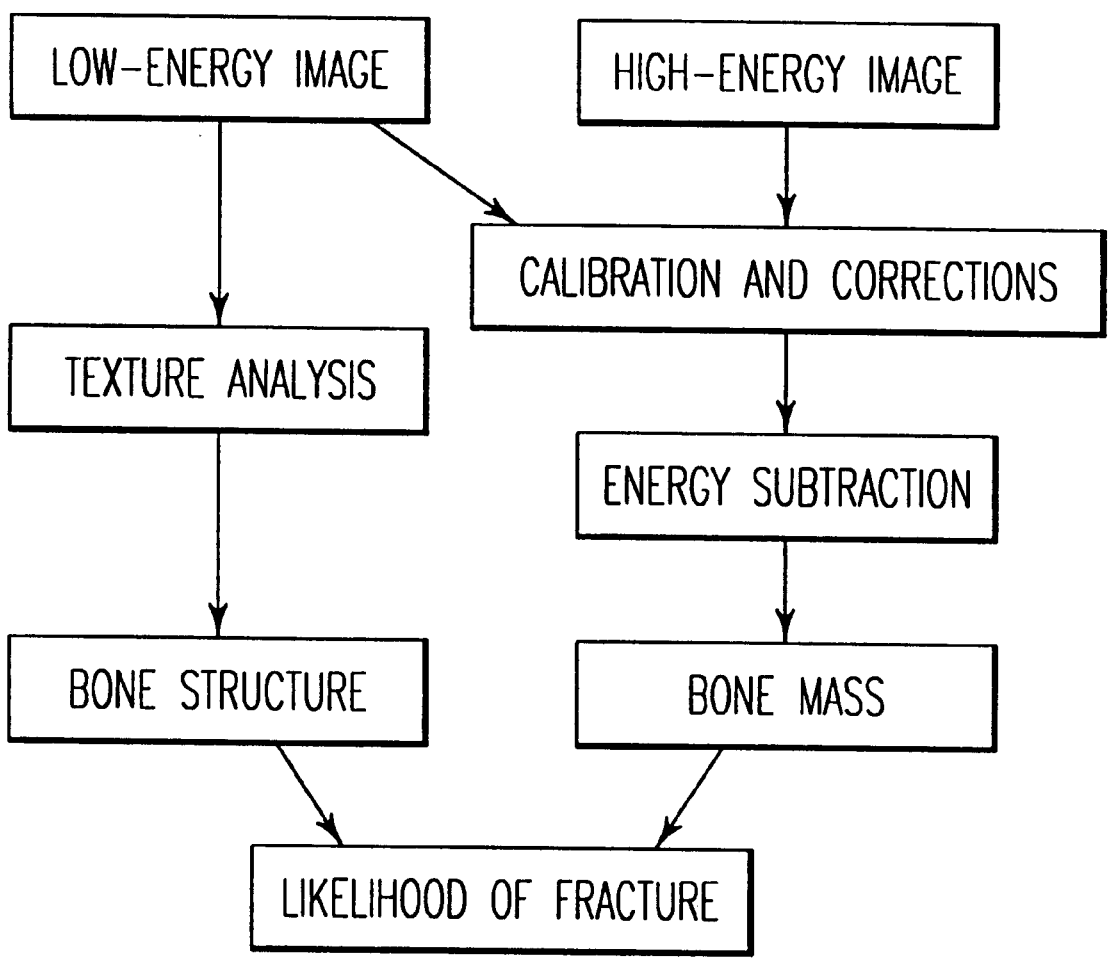
FIG. 21 is a schematic illustrating a method for the measurement of both bone density (bone mass) and bone structure from a single-projection, dual-energy radiographic image of the some bony body part such as the spine, hip or extremities according to the invention.

FIG. 21 is a schematic illustrating a method for the measurement of both bone density (bone mass) and bone structure from a single-projection, dual-energy radiographic image of some bony body part such as the spine, hip, or extremities according to the invention. Such a system produces a high-energy image and a low-energy image from either a "one shot" exposure technique that employs two detectors sandwich together or a "two-exposure" technique that utilizes two exposures to the patient. FIG. 22 is a schematic diagram illustrating two possible methods of obtaining the dual energy radiographic images. Such systems utilize "energy subtraction" techniques to yield "bone-cancelled" images and "soft-tissue-cancelled" images. Such "dual-energy" systems have been developed for moderately-high-spatial-resolution imaging of the soft tissue in chest and for very-low-spatial-resolution acquisition of bone mass (BMD) in, for example, the spine. However, such "dual-energy" systems have not been developed for moderately-high-spatial-resolution imaging of bone due to the large amount of quantum mottle that results in the bone image (i.e., the soft-tissue-cancelled image). Moderately high spatial resolution is desirable for the analysis of bone structure, though in the past, only bone mass was of interest, and thus, the low-resolution system were acceptable. However, now with the new method presented earlier in this invention application that yields measures of bone structure, it is desirable to have a system that can measure both bone mass and bone structure (as opposed to subjecting the patient to two examinations: one for bone mass (BMD) and one for bone structure (spine radiograph). The following presents such a system using computed radiography as the detector in the example. However, the method is not limited to computed radiography as the detector.

Computed radiography (CR) is a digital radiographic imaging system that uses plates consisting of BaFBr phosphor, a stimulable phosphor, to image the radiographic x-ray image. The pixel value in a CR image can be converted directly into x-ray exposure. The method uses dual-energy computed radiography (CR) imaging to obtain bone mass in a manner quite similar to that of DXA (BMD). Differences include a dependence on scatter due to the fact that conventional radiographic spine images are obtained with a broad area beam whereas the DXA scans are obtained with a low-resolution, pencil-beam geometry. However, the CR images are of high spatial resolution thus allowing for the low-energy image to be used for the texture measures of bone structure. Note that texture analysis is not possible on the tissue-cancelled images due to the presence of large quantum mottle (and the inability of increasing the exposure alot due to patient dose considerations). The measure for bone mass is performed in a way that the region on the bone image that encloses the spongiosa will be integrated. All this accomplished with just one examination.

In this example, dual-energy bone images of the spine, hip and extremeties are obtained using the CR system and the "one-shot" exposure technique (Ref 64). The method uses conventional x-ray equipment to produce "bone" and "soft tissue" images in exact temporal and spatial registration with a single x-ray exposure. Use of the one-shot technique eliminates motion artifacts between the high- and low-energy images and also avoids rapid switching of the x-ray tube voltage.

With the one-shot technique, it is advantageous for the input x-ray spectrum to be double peaked. Thus, K-edge filtration is used to a produce double-peaked x-ray spectrum. The CR plates consists of BaFBr phosphor, and thus the broad beam x-ray spectrum emitted from the x-ray tube is prefiltered so that the absorbed spectrum for the front CR plate will peak in the region of high barium attenuation coefficient. A prefilter of 300 mg/cm$^2$ gadolinium can be used. In order to compensate for the attenuation of the x-ray tube output by the K-edge prefilter, the tube loading (mAs) of the x-ray tube is increased.

Another filter is sandwiched between two imaging plates (made of the stimulable phosphor) having wide exposure-latitude characteristics. The front CR plate of the sandwich preferentially absorb low-energy x-ray photons and transmits high-energy photons. The high-energy photons are absorbed partially in the back plate yielding two simultaneously acquired images with different effective energies. The filter serves to increase the effective energy of the x-ray spectrum incident on the second imaging plate. Readily available materials for this filter are copper foil or the CR plates themselves (which contain barium). In the results presented later in this application, the filter consisted of two CR plates (200 mg/cm$^2$BaFBR) for this intermediate filtration.

Figure 23B:
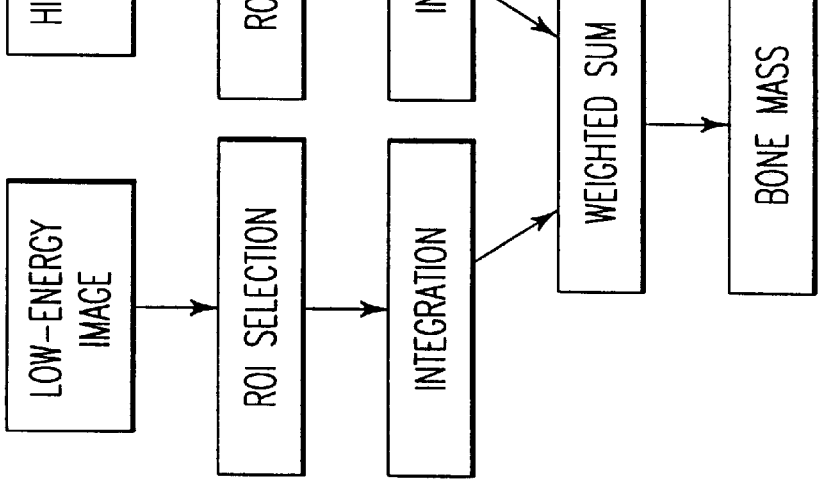
FIG. 23 is a schematic diagram illustrating two possible methods for energy subtraction as it relates to the measures of bone mass.
Figure 23A:
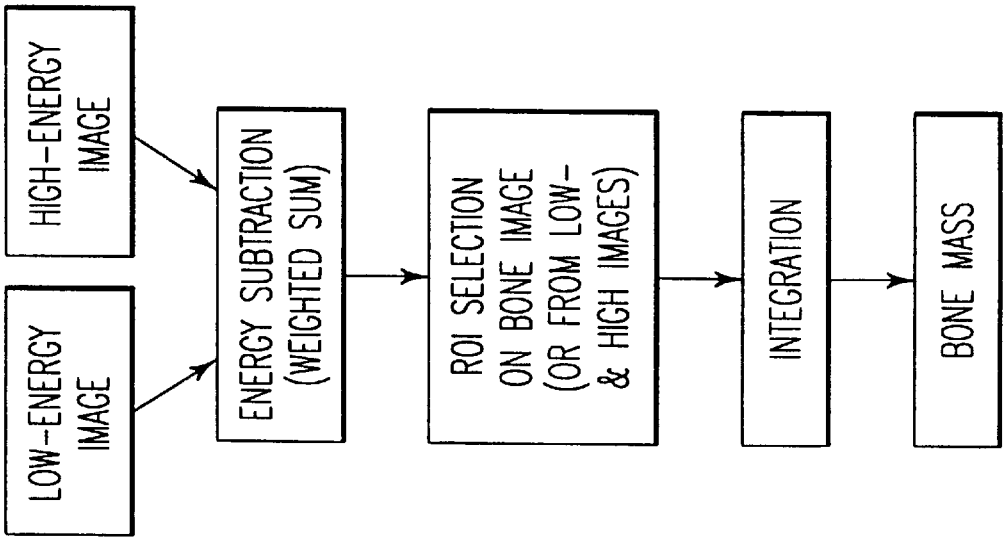

FIG. 23 is a schematic diagram illustrating two possible methods for energy subtraction as it relates to the measures of bone mass. In method A, the low-energy image and the high-energy images are first registered, passed through energy subtraction and then ROIs in the bone image that are within the vertebral body are integrated to yield a measure related to bone mass. In method B, the low-energy image and the high-energy image are each separately subjected to ROI placement and integration, and then a weighted sum of the two integrated values (with corrections for patient body size, scatter radiation present, etc.) is calculated to yield a measure related to bone mass. An advantage of method B, is that image registration in the conventional (high resolution)

sense is not necessary. However, a way (such as manual placement) to insure location of corresponding lumbar ROIs on the low and high energy images is necessary. In this application, are presented results using bone phantoms. The pair of digital images, obtained from the two CR plates in the sandwich cassette, are read digitally by the CR system.

Figure 24:
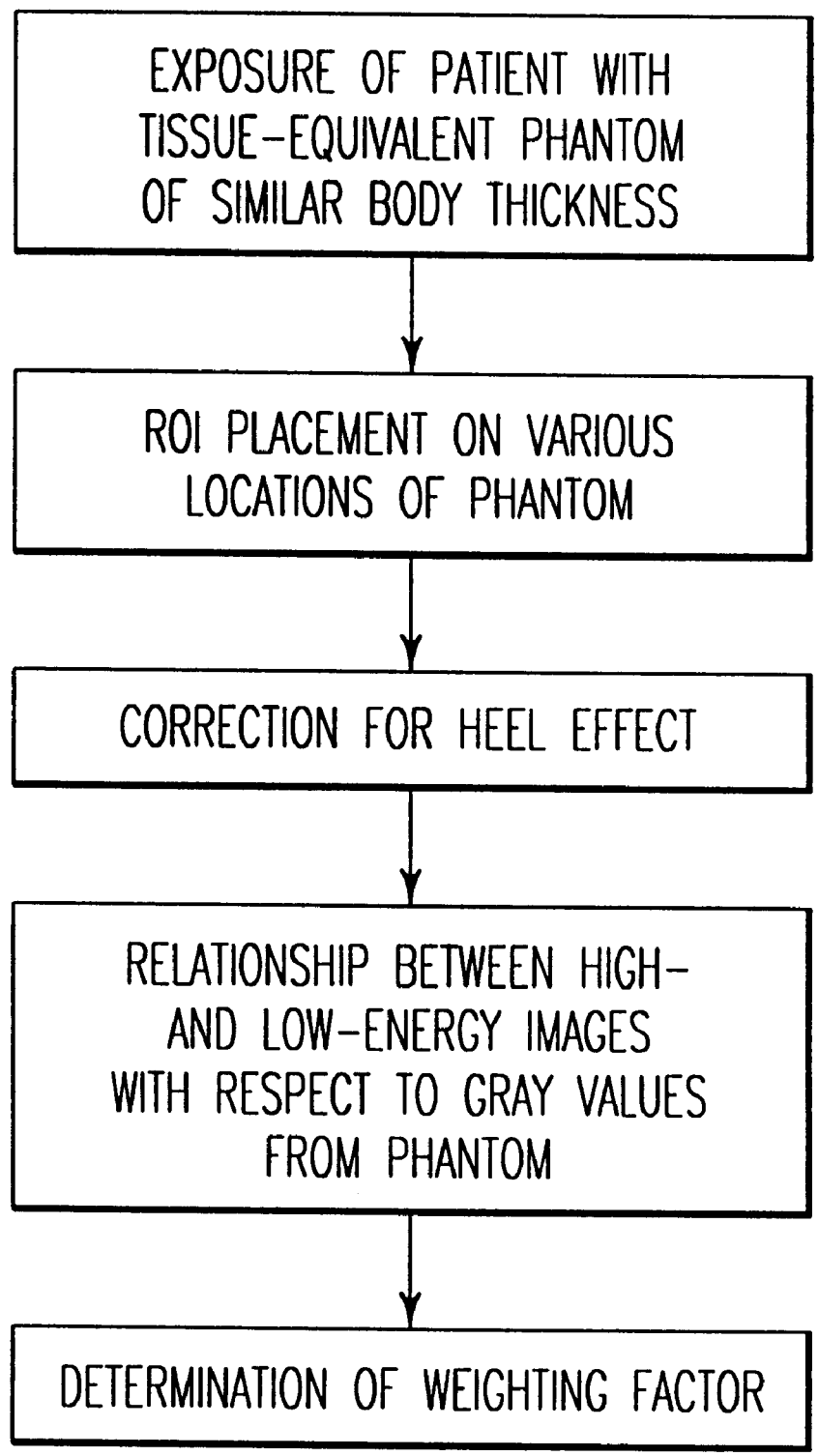
FIG. 24 is a schematic diagram illustrating one possible calibration method for measuring bone mass from dual-energy images, including compensation for the heel effect and calibration for body thickness.
Figure 25:
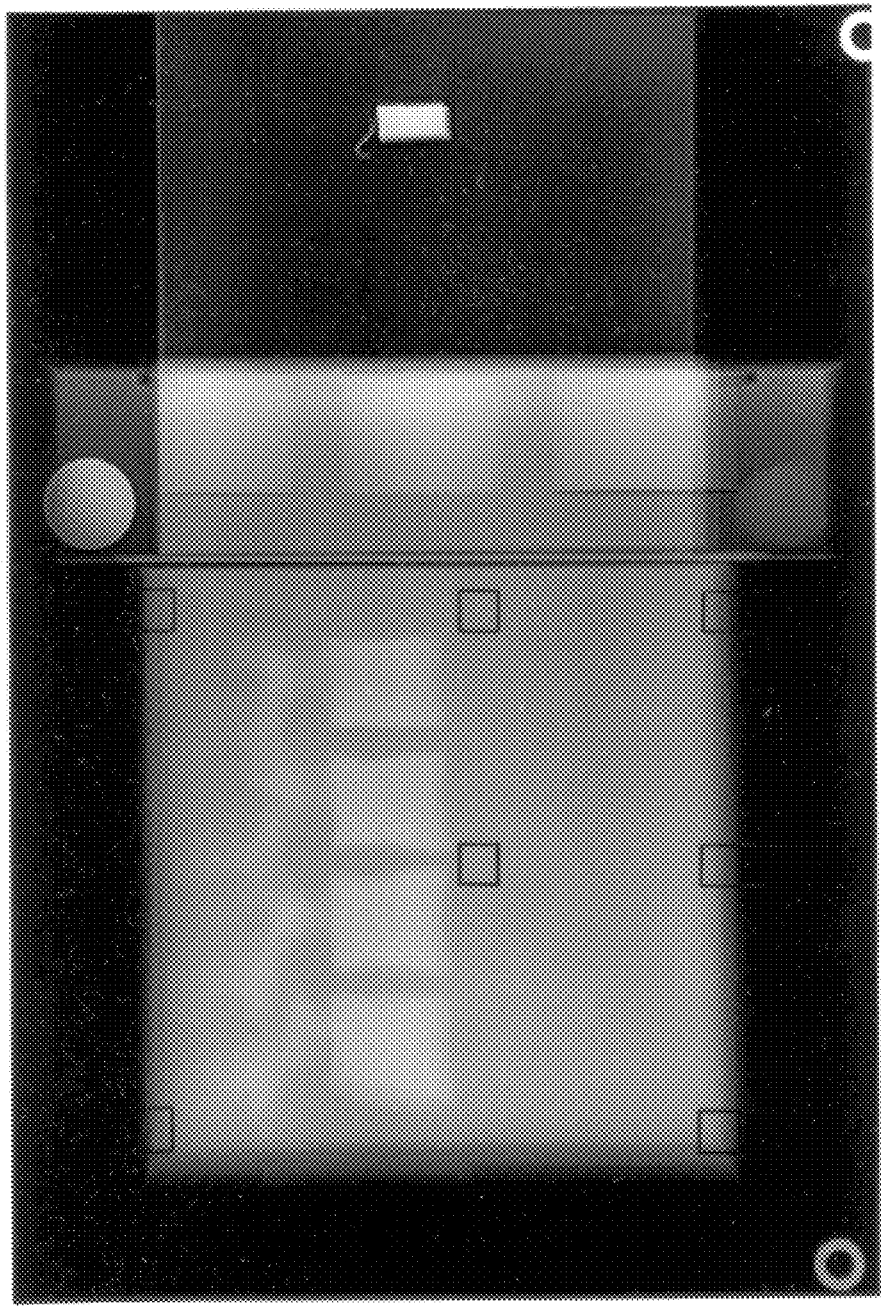
FIG. 25 is a schematic diagram illustrating a calibration phantom and its positioning during a patient exam.
Figure 26A:
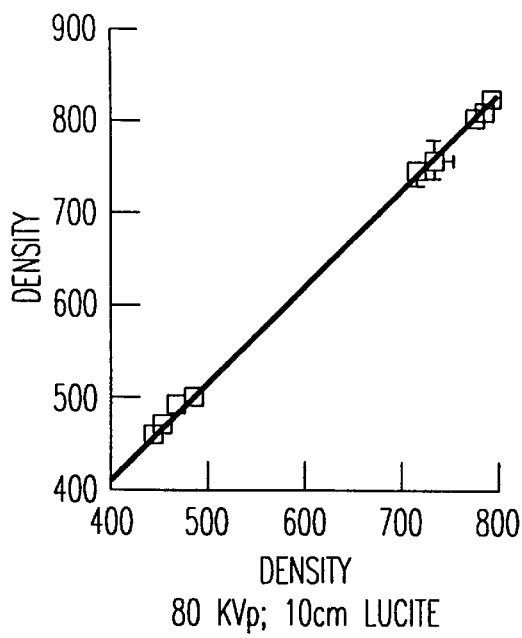
FIG. 26 is a graph showing the relationship between gray values obtained from low and high energy images of a lucite phantom; illustrating the calibration method.
Figure 26B:
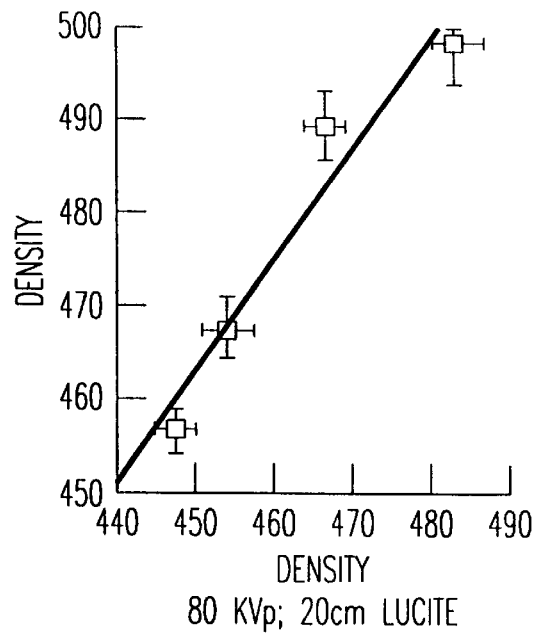
Figure 26C:
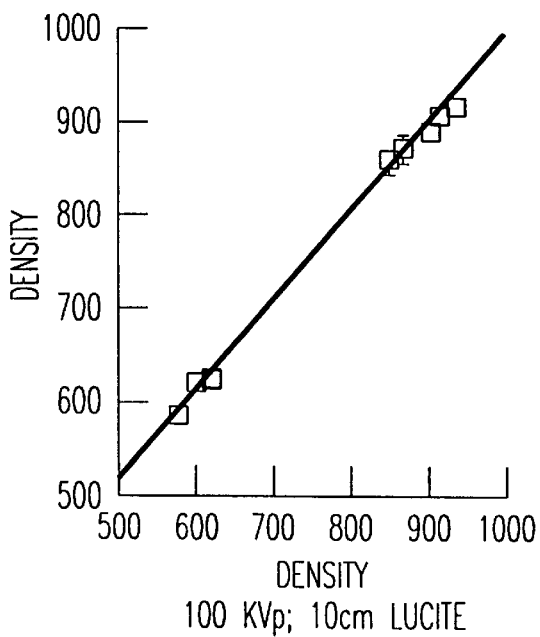
Figure 26D:
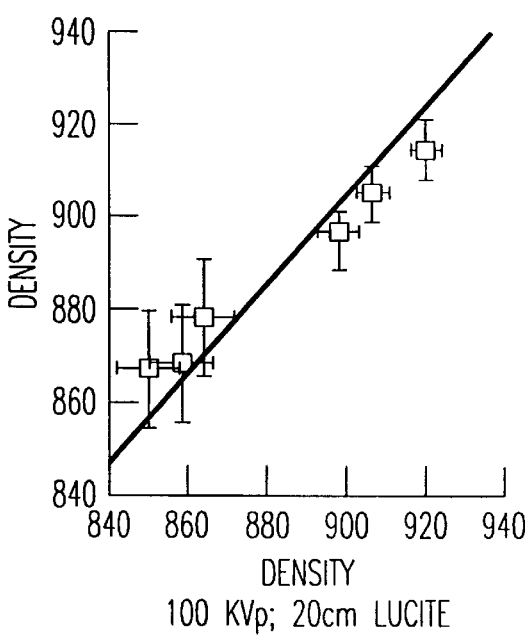

FIG. 24 is a schematic diagram illustrating one possible calibration method for measuring bone mass from dual-energy images, including compensation for the heel effect and calibration for body thickness. FIG. 25 is a schematic diagram illustrating a calibration phantom and its positioning during a patient exam. In the example, two phantoms were used. One of these phantoms is used to calibrate and consists of three cylinders of synthetic bone material. The other phantom was also made of synthetic bone, but was shaped to look like four lumbar vertebrae and encased in Lucite. Lucite was added to the top of the phantoms to simulated additional soft tissue, i.e., patients of varying thickness. The phantoms were imaged with the one-shot, dual-energy technique and quantities such as thickness of lucite and energy of the x-ray beam were varied in different trials.

FIG. 26 shows graphs of the relationship between gray values obtained from the low and high energy images of the phantom. The linear fit of these data is used to determine the weights for the weighted sum of the integrated value of the ROI on the low-energy image with that of the ROI on the high-energy image. Values from these graphs are then used in a look up table for different imaging techniques (i.e., kVp) and for patients of different thicknesses. The value obtained from the weighted sum is related to the bone mass. In a particular region of the image, both bone and soft tissue contribute to the attenuation of the x-ray beam. The amount proportional to the thickness of the bone can be determined by a weighted sum (or could be thought of as weighted subtraction), pixel by pixel, of the high and low energy image data, namely, $$B(x,y) = L(x,y) - W \cdot H(x,y),$$

where x,y is the location of the pixel, and L and H are the values in the low and high energy images, respectively, W is the weight determined from the slope of the linear fit, as demonstrated in FIG. 26. For bone mass, the integration of a region on a bone-only image is of interest. Thus, the method either does the weighted summation on the image data as shown in the above equation and then integrates on the noisy bone image (in which it may be difficult to define edges of the bone, such as the edge of the vertebral body) or integrates on the low-energy and high-energy images separately prior to the weighted summation, namely $$B = \text{sum over ROI of } [L(x,y)] - W \cdot \text{sum over ROI of } [H(x,y)],$$

where B here is proportional to the bone mass within the ROI. The edges of the vertebral bodies are easier delineated on both the low-energy and high-energy images, thus making locating the ROI easier.

Figure 27:
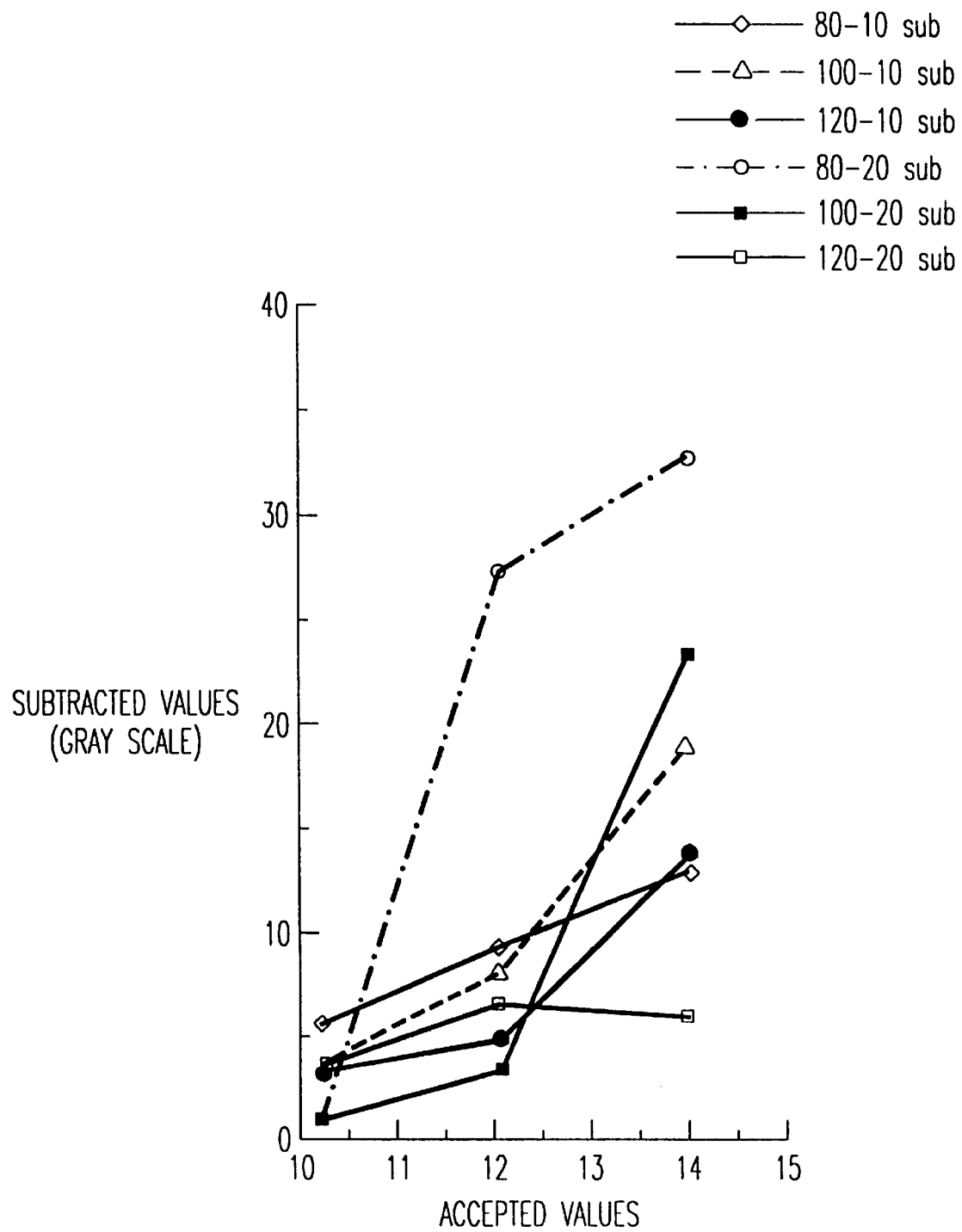
FIG. 27 is a graph showing the relationship between the measured values for bone mass (from a BMD phantom) and the accepted values for the particular phantom, and thus indicating the potential for using the technique for measuring bone mass (along with bone structure).

FIG. 27 is a graph showing the relationship between the measured values for bone mass (from a BMD phantom) and the accepted values for the particular phantom, and thus indicating the potential for using the technique for measuring bone mass. Since the measured values are not scaled, one can only look at the general trend of the data. The measured values from the weighted sum of the integrated ROIs from the low- and high-energy images follow the same order as does the BMD measures obtained from a Lunar DPX system. This is especially so in the images with only 10 cm of lucite on top of the phantom. Those with 20 cm were less stable, as expected due to increased scattering. This can be improved with the use of better antiscatter grids in the radiographic protocol or with a direct digital acquisition device (which have been shown to be 99% in scatter rejection).

The computerized texture analysis for bone structure (that was presented earlier in this application) is then performed on the low-energy images in order to measure the quality and architecture of the bone trabeculae. The texture measures are not determined on the bone images (i.e., tissue-cancelled images) since the large amount of radiographic mottle can "hide" the underlying texture of the bone structure. Thus, this dual-energy technique allows quantitation of both bone mass and bone structure, as demonstrated earlier in FIG. 21.

Figure 28:
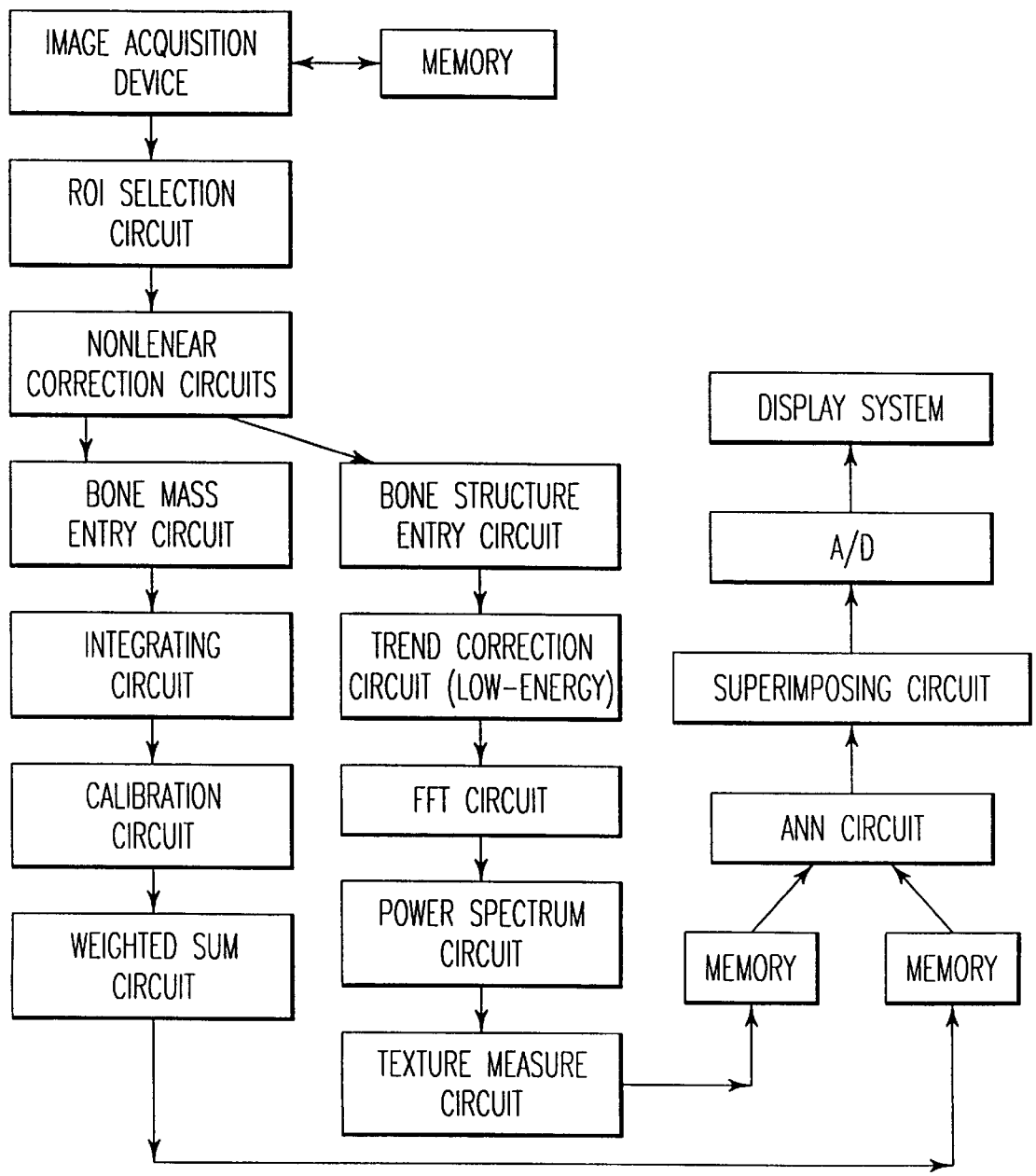
FIG. 28 is a schematic block diagram illustrating a system for implementing the method for the radiographic analysis of both bone mass and bone structure, and thus, risk of future fracture.

FIG. 28 is a more detailed schematic block diagram illustrating a system for implementing the method of the invention for analysis of both the bone mass and the bone trabecular structure. Referring to FIG. 28, two radiographic images (low-energy and high-energy) of an object are obtained from an image acquisition device and input to the system 2000. Each bone image is digitized and put into memory (2001). If the radiographic images are obtained with a direct digital device then there is no need for digitization. The image data are first passed through the ROI selection circuit (2002), the nonlinear detection system correction circuit (2003), and is then passed to the entry circuit for bone mass (2004) and to the entry circuit for bone structure (2005). For bone mass, the data are passed to the integration circuit (2006) and calibration circuit (2007). From there, the data are passed to the weighted sum circuit (2008) and saved in memory (2009). For bone structure, the data from the low-energy image are passed to the FFT circuit (2020) and the power spectrum circuit (2030). Power spectrum data are passed to the texture measure circuit (2040). Measures of both bone mass and bone structure are then passed to the ANN circuit (2050) in order to determine the likelihood for risk of future fracture, during which time the data are retained in image memory (2060). In the superimposing circuit (2070) the results are either superimposed onto images, stored in file format, or given in text format. The results are then displayed on the display system (2080) after passing through a digital-to-analog converter (2090).

Figure 29:
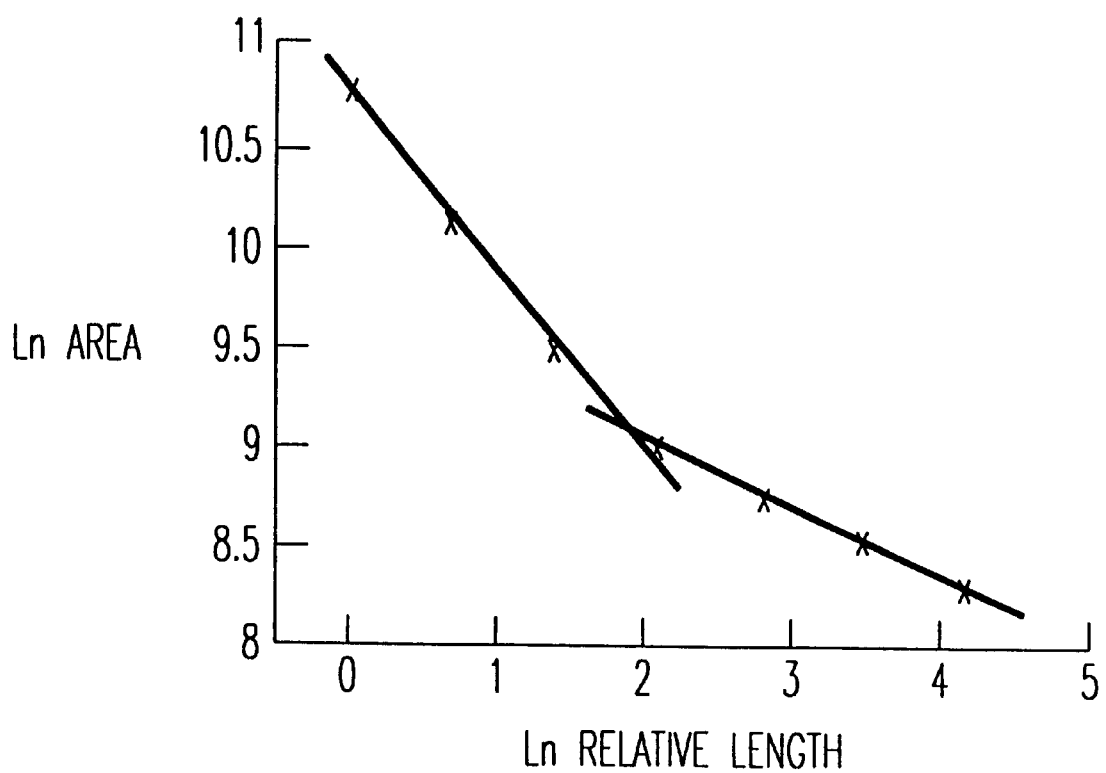
FIG. 29 illustrates the logarithmic relationship between "surface area" and effective pixel length for a ROI. Two distinct linear portions are demonstrated and each is fitted with a straight line of different slope, which is used to calculate fractal dimension.

Fractal analysis has also been preliminarily investigated as a means of analyzing the bone texture. Using the bone ROIs shown in FIG. 2, the surface area of each of the ROIs was computed at 7 different levels of resolution using pixel gray level analogously to height in the fractal calculations. Different levels of resolution (pixel length) were obtained by successively averaging larger and larger groups of adjacent pixels. FIG. 29 shows the log plot of surface area vs. pixel length for one ROI. The presence of the two distinct linear portions suggests a multifractal structure. Slopes of the overall graph of each ROI, as well as the slopes of each of the two portions of each graph were then used to obtain an estimate of the overall fractal dimension as well as an estimate of the fractal dimension at stronger and weaker levels of resolution corresponding to the 2 distinct portions of the graphs. Using ROC analysis with the fractal dimension of each ROI as the decision variable, the Az obtained using overall fractal dimension was 0.65, using the fractal dimension at the finer resolution portion was 0.76 and using the fractal dimension at the coarser resolution was 0.87 as compared to an Az of 0.6 obtained using BMD.

Multifractional analysis can also be used to characterize the bone texture within the ROIs. The fractal dimension of these ROIs will be estimated using a surface area technique, modified from one described for the computerized analysis of mammograms. The gray level of each pixel will be regarded as a "height" with pixel size as "length" and "width" to calculate a "surface area" for each ROI. Adjacent pixels will be then combined to yield an effectively larger pixel size with a new gray level averaged from these combined pixels. A new "surface area" will be calculated for each ROI, and the process will be successively repeated, combining adjacent pixels from earlier steps, and calculating the resultant surface area for each new effective pixel size. The fractal dimension (D) for each ROI is calculated, using:

$$D=2-H$$

where H is the slope of a least-squares line fitted to a plot of log surface area versus log pixel size for each ROI. The number 2 is the topological dimension of the gray level surface. The plot (as we have found) may exhibit a multi-fractal nature by indicating two linear regions—a textural (fine) fractal dimension and a structural (coarser) fractal dimension. Both the fine and the coarse fractal dimensions can be used as texture measures.

In two preliminary studies using separately the ROIs of the spine described above and ROIs from normal and osteoporotic hands, artificial neural networks (ANN) were employed. The input to the neural network was the normalized power spectrum data from the background-corrected ROI. Using ROIs of size 32 by 32 pixels, the successful ANN contained 512 (32*16) input units, 40 hidden units and one output unit. The value of the output unit served as the decision variable. The ANN was trained using an output of 1 for abnormal (osteoporotic) and 0 for normal. Using the 43 cases, the ANN successfully classified all abnormal ROIs as osteoporotic.

Artificial neural networks (ANN) can also be applied to the differentiation of texture patterns of bone trabeculae. ANN is a non-algorithmic approach to information processing. Unlike many artificial intelligence techniques, which require extensive knowledge of the many parameters involved, ANNs learn directly from examples that are provided repeatedly. Once trained, a neural network can distinguish among input patterns on the basis of its learning experience. The analysis of the texture patterns will be performed using the image data in the spatial frequency domain in order to eliminate the shift-variant nature of the image data. The ROIs will be evaluated by calculating the power spectra by Fourier transformation of the background-corrected ROIs and scaled. The scaled power spectra will then be used as input to the neural network. Thus, for ROIs of size 32 by 32 pixels, the resulting number of input units is 16 by 32; due to the symmetry in the Fourier transformation and subsequent calculation of the power spectrum. A three-layer, feed-forward neural network can be used with one output unit. A back-propagation algorithm with generalized delta rule will be employed in the training process. The input, which corresponds to the corresponding power spectrum, is provided to the input layer of the neural network. The desired output (truth) is provided to the output layer during the training process. The hidden layer, which is the key element in mapping of the input patterns to the output values, is located between the input and output layers. A nonlinear logistic function will be used as the activation function for each processing unit in the neural network, in which $$O_{pj} = \frac{1}{1 + \exp\left(\sum_i w_{ji} o_{pi} + \theta_j\right)}$$

where $o_{pj}$ is the jth element of the actual output pattern produced by the presentation of input patter p, $w_{ji}$ is the weight from the ith to jth units, and $\theta j$ is the threshold of the jth units. in the training process, the internal parameters of the connections between layers (including threshold values of each unit) are adjusted iteratively so that the difference between the output values and the desired results is minimized. This can be accomplished by the following rule:

$$\Delta w_{ji}(n+1)=\eta(\delta_p \rho_{pi})+\alpha \Delta w_{ji}(n),$$

where n indexes the number of iterations, $\eta$ is the learning rate, $\delta_{pi}$ is the error signal, which is related to the difference between the output of the neural network and the desired output, and $\alpha$ is a momentum term that determines the effect of past weight changes on the current direction of movement in weight space. The desired "truth" for use in training the ANN will initially be either a 1 or a 0, where 1 corresponds to the patient having a fracture elsewhere in the spine and 0 corresponding to the patient not having such a fracture.

Obviously, numerous modifications and variations of the present invention are possible in light of the above technique. It is therefore to be understood that within the scope of the appended claims the invention may be practiced otherwise than as specifically described herein. although the current application is focused on radiographic medicinal images, the concept can be expanded to segmentation in other images of the human body.

What is claimed as new and desired to be secured by Letters Patent of the United States is:

1. A method for analyzing bone, comprising:
   obtaining an image containing said bone;
   selecting a region of interest of said bone;
   determining at least one texture measure of said region of interest of said bone; and
   analyzing said bone using said at least one texture measure.

2. A method as recited in claim 1, comprising:
   background-trend correcting said region of interest to produce a background-trend corrected region of interest; and
   determining said at least one texture measure of said background-trend corrected region of interest.

3. A method as recited in claim 1, wherein selecting said region of interest comprises:
   selecting said region of interest on at least one vertebral body in a spine.

4. A method as recited in claim 1, wherein determining said at least one texture measure comprises:
   determining a power spectrum of said region of interest; and
   determining said at least one texture measure using said power spectrum.

5. A method as recited in claim 4, comprising:
   dividing said power spectrum into a number of sectors; and
   determining said at least one texture measure for each of said sectors.

6. A method as recited in claim 4, wherein determining said at least one texture measure comprises:

determining a root mean square variation and a first moment of said power spectrum.

7. A method as recited in claim 6, comprising:
filtering said power spectra;
determining said root mean square variation as R:

$$R = \sqrt{\int_{-\infty}^{\infty}\int_{-\infty}^{\infty} V^2(u,v)|F(u,v)|^2 \, du\, dv}$$

determining said first moment as M:

$$M = \frac{\int_{-\infty}^{\infty}\int_{-\infty}^{\infty} \sqrt{u^2+v^2}\, V^2(u,v)|F(u,v)|^2\, du\, dv}{\int_{-\infty}^{\infty}\int_{-\infty}^{\infty} V^2(u,v)|F(u,v)|^2\, du\, dv}$$

where:
V(u,v) is a filter function; and
F(u,v) is said power spectrum.

8. A method as recited in claim 7, comprising:
determining an angular dependence Rθ of said variation R:

$$R_\Theta(\Theta_1 \leq \Theta < \Theta_2) = \sqrt{\sum_m \sum_n |F_{m,n}|^2} \text{ for } \Theta_1 \leq \tan^{-1}\left(\frac{n}{m}\right) < \Theta_2$$

determining an angular dependence Mθ of said first moment M:

$$M_\Theta(\Theta_1 \leq \Theta < \Theta_2) = \frac{\sum_m \sum_n \sqrt{m^2+n^2}\, |F_{m,n}|^2}{\sum_m \sum_n |F_{m,n}|^2} \text{ for } \Theta_1 \leq \tan^{-1}\left(\frac{n}{m}\right) < \Theta_2.$$

for $\Theta_1 \leq \tan^{-1}(n/m) < \Theta_2$.

9. A method as recited in claim 8, comprising:
dividing said power spectrum into a number of sectors; and
determining said angular dependence of said variation and said angular dependence of M for each of said sectors.

10. A method as recited in claim 9, comprising:
determining a minimum of said angular dependence of M.

11. A method as recited in claim 4, wherein determining said at least one texture measure comprises:
determining a root mean square variation of said power spectrum;
determining an angular dependence of said variation;
determining a maximum of said angular dependence;
determining a minimum of said angular dependence;
determining a standard deviation of said variation; and
determining a relative standard deviation of said variation.

12. A method as recited in claim 11, comprising:
inputting selected of said variation, said angular dependence of said variation, said maximum of said angular dependence, said minimum of said angular dependence, said standard deviation of said variation and said relative standard deviation of said variation into a discriminator; and
determining a likelihood of risk of fracture using said discriminator.

13. A method as recited in claim 4, wherein determining said at least one texture measure comprises:
determining a first moment of said power spectrum;
determining an angular dependence of said first moment;
determining a maximum of said angular dependence;
determining a minimum of said angular dependence;
determining a standard deviation of said first moment; and
determining a relative standard deviation of said first moment.

14. A method as recited in claim 13, comprising:
inputting selected of said first moment, said angular dependence of said first moment, said maximum of said angular dependence, said minimum of said angular dependence, said standard deviation of said first moment and said relative standard deviation of said first moment into a discriminator; and
determining a likelihood of risk of fracture using said discriminator.

15. A method as recited in claim 4, comprising:
determining a second power spectrum of a uniform tissue region in said image; and
normalizing said power spectrum using said second power spectrum.

16. A method as recited in claim 15, comprising:
performing edge gradient analysis on said region of interest; and
determining a maximum cumulative edge gradient.

17. A method as recited in claim 4, comprising:
inputting said at least one texture measure into a discriminator; and
determining a likelihood of risk of fracture using said discriminator.

18. A method as recited in claim 1, comprising:
obtaining a spine image;
selecting said region of interest in a vertebral body; and
determining a trabecular pattern in said vertebral body.

19. A method as recited in claim 18, comprising:
background-trend correcting said region of interest.

20. A method as recited in claim 18, wherein determining said trabecular pattern comprises:
determining a power spectrum of said region of interest; and
determining said at least one texture measure using said power spectrum.

21. A method as recited in claim 20, comprising:
dividing said power spectrum into a number of sectors; and
determining said at least one texture measure for each of said sectors.

22. A method as recited in claim 21, wherein determining said at least one texture measure comprises:
determining a root mean square variation and a first moment of said power spectrum.

23. A method as recited in claim 18, wherein determining said at least one texture measure comprises:
determining a root mean square variation and a first moment of said power spectrum.

24. A method as recited in claim 18, comprising:
performing edge gradient analysis on said region of interest; and
determining a maximum cumulative edge gradient.

25. A method as recited in claim 18, comprising:

inputting said at least one features into a discriminator; and determining a likelihood of risk of fracture of using said discriminator.

26. A method as recited in claim 1, comprising:

obtaining a second image of said bone;

selecting a second region of interest in said second image;

determining bone mass based on said region of interest and said second region of interest; and analyzing said bone based on said bone mass and said texture measure.

27. A method as recited in claim 26, wherein determining said bone mass comprises:

integrating said region of interest to obtain a first integration value;

integrating said second region of interest to obtain a second integration value; and determining a weighted sum of said first and second integration values.

28. A method as recited in claim 26, comprising:

obtaining said image and said second image such that each has a plurality of pixels with a gray level value; and determining a linear fit from said gray level values of said image and said second image.

29. A method as recited in claim 28, comprising:

determining a first sum of gray levels of first pixels in said image over said region of interest;

determining a second sum of gray levels of second pixels in said second image over said second region of interest; and determining said bone mass based on said first and second sums and said linear fit.

30. A method as recited in claim 26, comprising:

obtaining said image at a first energy level and having a plurality of first gray-level pixels;

obtaining said second image at a second energy level higher than said first energy level and having a plurality of second gray-level pixels;

integrating said image using said region of interest to obtain a first integration value;

integrating said second image using said second region of interest to obtain a second integration value;

determining a linear fit from said first and second gray-level pixels;

determining first and second weighted sums of said first and second integration values; and determining said bone mass using said first and second weighted sums and said linear fit.

31. A method as recited in claim 26, comprising:

inputting said at least one texture measure and said bone mass into a discriminator; and determining a likelihood of risk of fracture using said discriminator.

32. A method as recited in claim 31, wherein:

determining said at least one texture measure comprises:
 determining a power spectrum of said region of interest; and
 determining a root mean square variation and a first moment of said power spectrum; and determining said bone mass comprises:
 integrating said region of interest to obtain a first integration value;
 integrating said second region of interest to obtain a second integration value; and
 determining a weighted sum of said first and second integration values.

33. A method as recited in claim 1, comprising:

selecting said region of interest having a plurality of gray level pixels; and determining a surface area of said region of interest at each of a plurality of levels of resolution.

34. A method as recited in claim 33, wherein determining said surface area comprises:

determining a slope using said surface areas and said levels of resolution;

determining a fractal dimension using said slope.

35. A method as recited in claim 34, comprising:

determining said fractal dimension D=2−H, where H is said slope.

36. A method as recited in claim 33, comprising:

determining a first surface area of said region of interest based upon said pixels;

selectively combining said pixels to obtain combined pixels;

determining a second surface area based upon said combined pixels; and determining a fractal dimension based upon said first and second surface areas.

37. A method as recited in claim 36, comprising:

determining a slope using said first and second surface areas and said levels of resolution; and determining said fractal dimension D=2−H, where H is said slope.

* * * * *